United States Patent
Smith et al.

(10) Patent No.: US 12,060,448 B2
(45) Date of Patent: Aug. 13, 2024

(54) COMPOSITIONS INCLUDING FUNCTIONAL GROUPS COUPLED TO SUBSTRATES, AND METHODS OF MAKING THE SAME

(71) Applicants: ILLUMINA, INC., San Diego, CA (US); ILLUMINA CAMBRIDGE LIMITED, Cambridge (GB)

(72) Inventors: Randall Smith, San Marcos, CA (US); Wayne George, Ilford (GB); Andrew Brown, Cambridge (GB)

(73) Assignees: Illumina, Inc., San Diego, CA (US); Illumina Cambridge Limited, Cambridge (GB)

( * ) Notice: Subject to any disclaimer, the term of this patent is extended or adjusted under 35 U.S.C. 154(b) by 395 days.

(21) Appl. No.: 17/565,818

(22) Filed: Dec. 30, 2021

(65) Prior Publication Data

US 2022/0220242 A1  Jul. 14, 2022

Related U.S. Application Data

(60) Provisional application No. 63/133,955, filed on Jan. 5, 2021.

(51) Int. Cl.
  *C08J 7/12* (2006.01)
  *C07H 21/00* (2006.01)
  (Continued)

(52) U.S. Cl.
  CPC ........... *C08F 222/40* (2013.01); *C07H 21/00* (2013.01); *C08F 283/12* (2013.01); *C08J 7/12* (2013.01);
  (Continued)

(58) Field of Classification Search
  CPC ........... C07H 21/00; C08F 222/40; C08J 7/12
  See application file for complete search history.

(56) References Cited

U.S. PATENT DOCUMENTS 7,427,667 B2   9/2008  Goddard et al.
9,012,022 B2 *  4/2015  George ............... C12Q 1/6806
                                          428/407
(Continued)

FOREIGN PATENT DOCUMENTS

EP   2319854 A1    5/2011
WO   9847910 A1   10/1998
(Continued)

OTHER PUBLICATIONS

International Search Report and Written Opinion for PCT/US2021/065625 dated Apr. 26, 2022; 13 pages.
Mondal et al., "Macromolecular engineering in functional polymers via 'click chemistry' using triazolinedione derivatives" Progress in Polymer Science; 113: 1-28 (2020) https://doi.org/10.1016/j.progpolymsci.2020.101343.
(Continued)

*Primary Examiner* — Michael P Wieczorek
(74) *Attorney, Agent, or Firm* — Sheppard, Mullin, Richter & Hampton LLP; Jaime D. Choi

(57) ABSTRACT

In one example, an unsaturated cyclic dione is coupled to the substrate, and is reacted with an indole or indazole including a first functional group to form a first adduct coupling the first functional group to the substrate. In another example, an unsaturated cyclic dione is coupled to a substrate and reacted with a diene including a functional group to form an adduct coupling the functional group to the substrate. In another example, an indole or indazole is coupled to a substrate, and is reacted with an unsaturated cyclic dione including an oligonucleotide to form an adduct coupling the oligonucleotide to the substrate. In another example, a diene is coupled to a substrate, and is reacted with an unsaturated cyclic dione including an oligonucleotide to form an adduct coupling the oligonucleotide to the substrate.

22 Claims, 13 Drawing Sheets

Specification includes a Sequence Listing.

(51) Int. Cl.
    *C08F 222/40*     (2006.01)
    *C08F 283/12*     (2006.01)
    *C12N 15/10*     (2006.01)

(52) U.S. Cl.
    CPC ...... *C12N 15/1006* (2013.01); *C12N 2310/51* (2013.01)

(56) References Cited

U.S. PATENT DOCUMENTS

| | | |
|---|---|---|
| 2014/0079923 A1 | 3/2014 | George et al. |
| 2016/0122816 A1 | 5/2016 | Brown et al. |

FOREIGN PATENT DOCUMENTS

| | | |
|---|---|---|
| WO | 2014133905 A1 | 9/2014 |
| WO | 2017/007753 A1 | 1/2017 |
| WO | 2018118932 A1 | 6/2018 |
| WO | 2018119053 A1 | 6/2018 |

OTHER PUBLICATIONS

Mondal et al., "Thermally amendable tailor-made acrylate copolymers via RAFT polymerization and ultrafast alder-ene "click" chemistry" Journal of Polymer Science Part A: Polymer Chemistry; 56(20); 2310-2318 (2018).

Billiet et al. "Triazolinediones enable ultrafast and reversible click chemistry for the design of dynamic polymer systems"; Nature Chemistry; vol. 6; Sep. 2014; 815-821.

Houck et al. "Design of a thermally controlled sequence of triazolinedione-based click and transclick reactions"; Chem. Sci., 2017, 8, 3098-3108.

Kehagias et al. "Stamp replication for thermal and UV nanoimprint lithography using a UV-sensitive silsesquioxane resist" Microelectronic Engineering; 86: 776-778 (2009).

Xiao et al. "Efficient Metal-Free "Grafting Onto" Method for Bottlebrush Polymers by Combining RAFT and Triazolinedione-Diene Click Reaction"; American Chemical Society; Macromolecules 2016, 49, 4452-4461.

* cited by examiner

SEQUENCE LISTING

<160> NUMBER OF SEQ ID NOS: 4

<210> SEQ ID NO 1
<211> LENGTH: 29
<212> TYPE: DNA
<213> ORGANISM: Artificial Sequence
<220> FEATURE:
<223> OTHER INFORMATION: Primer P5 - Paired read

<400> SEQUENCE: 1
aatgatacgg cgaccaccga gauctacac        29

<210> SEQ ID NO 2
<211> LENGTH: 24
<212> TYPE: DNA
<213> ORGANISM: Artificial Sequence
<220> FEATURE:
<223> OTHER INFORMATION: Primer P7 - Paired read
<220> FEATURE:
<221> NAME/KEY: misc_feature

```
<222> LOCATION: (22)..(22)
<223> OTHER INFORMATION: n = G or 8-oxoguanine

<400> SEQUENCE: 2
caagcagaag acggcatacg anat                                          24

<210> SEQ ID NO 3
<211> LENGTH: 20
<212> TYPE: DNA
<213> ORGANISM: Artificial Sequence
<220> FEATURE:
<223> OTHER INFORMATION: Primer P5 - Single read

<400> SEQUENCE: 3
aatgatacgg cgaccaccga                                               20

<210> SEQ ID NO 4
<211> LENGTH: 21
<212> TYPE: DNA
<213> ORGANISM: Artificial Sequence
<220> FEATURE:
<223> OTHER INFORMATION: Primer P7 - Single read

<400> SEQUENCE: 4
caagcagaag acggcatacg a                                             21
```

COMPOSITIONS INCLUDING FUNCTIONAL GROUPS COUPLED TO SUBSTRATES, AND METHODS OF MAKING THE SAME

CROSS-REFERENCE TO RELATED APPLICATIONS

This application claims the benefit of U.S. Provisional Patent Application No. 63/133,955, filed Jan. 5, 2021 and entitled "Compositions Including Functional Groups Coupled to Substrates, and Methods of Making the Same," the entire contents of which are incorporated by reference herein.

FIELD

This application relates to coupling functional groups to substrates.

SEQUENCE LISTING

The instant application contains a Sequence Listing which has been submitted electronically in ASCII format and is hereby incorporated by reference in its entirety. Said ASCII copy, created on Mar. 23, 2022, and is named 8549101900_SL.txt and is 1,229 bytes in size.

BACKGROUND

Polymer-coated substrates are used in many technological applications. For example, implantable medical devices can be coated with biologically inert polymers. In another example, polymer-coated substrates are used for the preparation and/or analysis of biological molecules. Molecular analyses, such as certain nucleic acid sequencing methods, rely on the attachment of nucleic acid strands to a polymer-coated surface of a substrate. The sequences of the attached nucleic acid strands can then be determined by a number of different methods that are known in the art.

In certain sequencing processes, such as sequencing-by-synthesis (SBS), a surface of a substrate, such as a flow cell, is coated with a polymer to which oligonucleotide primers (e.g., single stranded DNA or ssDNA) are then grafted.

The polymer surfaces (and their preparation) are generally compatible with a wide range of sequencing and detection processes, including different chemical conditions, temperatures, optical detection methods, capture moiety densities, and other parameters, and are generally stable under various storage and shipping conditions. Certain polymer materials used in these molecular biology approaches employ pendant azido groups that are reacted in a copper-mediated cycloaddition reaction with alkene or alkyne groups on the surface of a substrate and/or oligonucleotides to be grafted. Residual copper, however, can have cytotoxic effects in biologically-relevant environments. With respect to DNA sequencing applications, in some instances copper can damage DNA, thereby reducing sequencing yield and data quality. In addition, often copper-catalyzed reactions are copper-intensive, and therefore are expensive, and may not run efficiently or quickly enough to ensure adequate polymer attachment and localization on a substrate surface. Thus, there is a need for surface polymer coatings with improved properties, such as increased reaction efficiency and that lead to reduced residual copper.

SUMMARY

Examples provided herein are related to compositions including functional groups coupled to substrates, and methods of making the same. Methods of using such compositions also are disclosed.

Some examples herein provide method of coupling a functional group to a substrate. The method may include providing an unsaturated cyclic dione coupled to a substrate, and reacting the unsaturated cyclic dione with an indole or indazole including a first functional group to form a first adduct coupling the first functional group to the substrate.

In some examples, the unsaturated cyclic dione is:

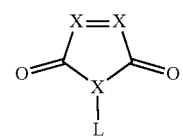

where L includes a linker to the substrate and each X independently is CH or N. In some examples, the unsaturated cyclic dione is triazolinedione:

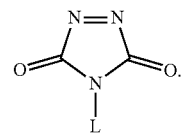

In some examples, the unsaturated cyclic dione is maleimide:

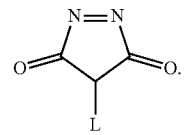

In some examples, 5. The method of claim 2, wherein the unsaturated cyclic dione is 4-cyclopentene-1,3-dione:

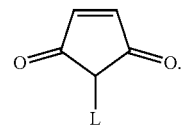

In some examples, the indole or indazole is:

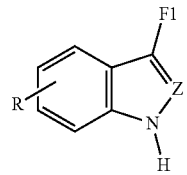

where F1 includes the first functional group; R is H, an electron withdrawing group, or an electron donating group; and Z is CH or N. In some examples, the indole is 1H-indole:

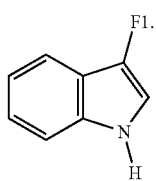

In some examples, the indole is 1H-indazole:

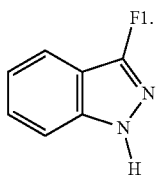

In some examples, the first adduct is:

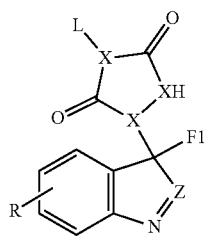

where L includes a linker to the substrate and each X independently is CH or N. In some examples, the first adduct is:

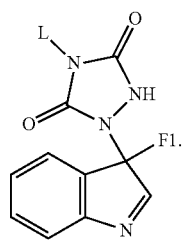

In some examples, the method further includes heating the first adduct to regenerate the cyclic unsaturated dione coupled to the substrate.

In some examples, the method further includes reacting the first adduct with a diene including a second functional group to form a second adduct coupling the second functional group to the substrate. In some examples, the diene includes a 1,3-diene. In some examples, the 1,3-diene is:

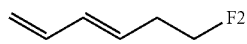

where F2 includes the second functional group. In some examples, the second adduct is:

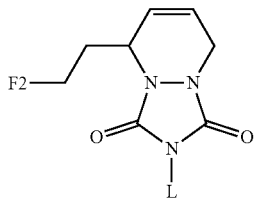

where L includes a linker to the substrate.

In some examples, the second functional group is selected from the group consisting of: an oligonucleotide, a hydrophilic molecule, a hydrophilic macromolecule, a catalyst, and a label. In some examples, the second functional group is an oligonucleotide.

In some examples, the first functional group is selected from the group consisting of: an oligonucleotide, a hydrophilic molecule, a hydrophilic macromolecule, a catalyst, and a label. In some examples, the first functional group is an oligonucleotide.

In some examples, the substrate includes a polymer disposed on a solid support. In some examples, the polymer is functionalized to include polyhedral oligomeric silsesquioxane (POSS).

In some examples, providing the unsaturated cyclic dione coupled to the substrate includes: providing a 4-substituted urazole coupled to the substrate, and oxidizing the 4-substituted urazole to form a triazolinedione.

Some examples herein provide a composition that includes a substrate, and an adduct coupled to the substrate:

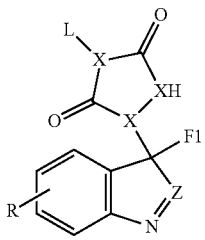

where L includes a linker to the substrate; F1 includes a first functional group; each X independently is CH or N; R is H, an electron withdrawing group, or an electron donating group; and Z is CH or N.

In some examples, the adduct is:

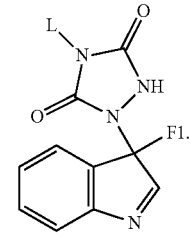

In some examples, the first functional group is selected from the group consisting of: an oligonucleotide, a hydrophilic molecule, a hydrophilic macromolecule, a catalyst, and a label. In some examples, the first functional group is an oligonucleotide.

In some examples, the substrate includes a polymer disposed on a solid support. In some examples, the polymer is functionalized to include polyhedral oligomeric silsesquioxane (POSS).

Some examples herein provide method of coupling a functional group to a substrate. The method may include providing an unsaturated cyclic dione coupled to a substrate, and reacting the unsaturated cyclic dione with a diene including a functional group to form an adduct coupling the functional group to the substrate.

In some examples, the unsaturated cyclic dione is:

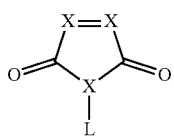

where L is a linker to the substrate and each X independently is CH or N. In some examples, the unsaturated cyclic dione is triazolinedione:

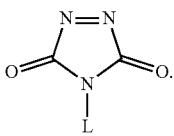

In some examples, the unsaturated cyclic dione is maleimide:

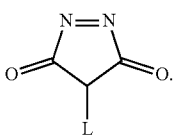

In some examples, the unsaturated cyclic dione is 4-cyclopentene-1,3-dione:

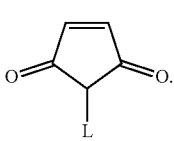

In some examples, the diene includes a 1,3-diene. In some examples, the 1,3-diene is:

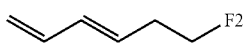

where F2 includes the functional group. In some examples, the adduct is:

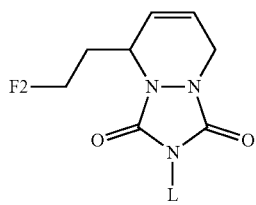

where L includes a linker to the substrate.

In some examples, the functional group is selected from the group consisting of: an oligonucleotide, a hydrophilic molecule, a hydrophilic macromolecule, a catalyst, and a label. In some examples, the functional group is an oligonucleotide.

In some examples, the substrate includes a polymer disposed on a solid support. In some examples, the polymer is functionalized to include polyhedral oligomeric silsesquioxane (POSS).

In some examples, providing the unsaturated cyclic dione coupled to the substrate includes: providing a 4-substituted urazole coupled to the substrate, and oxidizing the 4-substituted urazole to form triazolinedione.

Some examples herein provide a composition that includes a substrate, and an adduct coupled to the substrate:

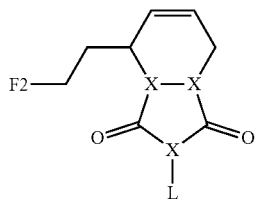

where L includes a linker to the substrate, F2 includes a functional group, and each X independently is CH or N.

In some examples, the adduct is:

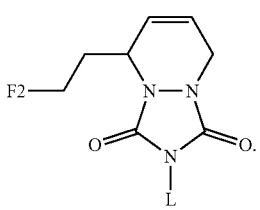

In some examples, the adduct is:

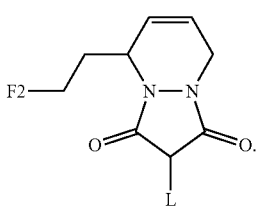

In some examples, the adduct is:

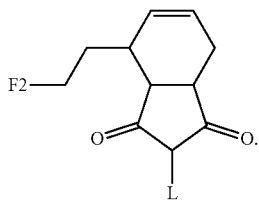

In some examples, the functional group is selected from the group consisting of: an oligonucleotide, a hydrophilic molecule, a hydrophilic macromolecule, a catalyst, and a label. In some examples, the functional group is an oligonucleotide.

In some examples, the substrate includes a polymer disposed on a solid support. In some examples, the polymer is functionalized to include polyhedral oligomeric silsesquioxane (POSS).

Some examples herein provide a method of coupling a functional group to a substrate. The method may include providing an indole or indazole coupled to a substrate, and reacting the indole or indazole with a first unsaturated cyclic dione including an oligonucleotide to form a first adduct coupling the oligonucleotide to the substrate.

In some examples, the first unsaturated cyclic dione is:

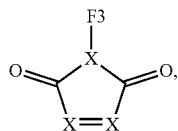

wherein F3 includes the oligonucleotide and each X independently is CH or N. In some examples, the first unsaturated cyclic dione is triazolinedione:

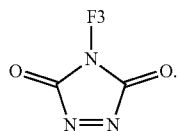

In some examples, the indole or indazole is:

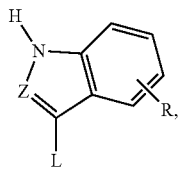

where Z is CH or N, L includes a linker to the substrate, and R is H, an electron withdrawing group, or an electron donating group. In some examples, the indole is 1H-indole:

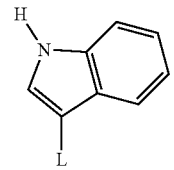

where L is a linker to the substrate. In some examples, the first adduct is:

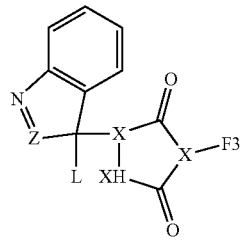

wherein F3 includes the oligonucleotide, and each X independently is CH or N.

In some examples, the method further includes heating the first adduct to regenerate the indole or indazole coupled to the substrate. In some examples, the method further includes, after regenerating the indole or indazole coupled to the substrate, reacting the indole or indazole with a second unsaturated cyclic dione to form a second adduct. In some examples, the second unsaturated cyclic dione includes a functional group. In some examples, the functional group is selected from the group consisting of: a second oligonucleotide, a hydrophilic molecule, a hydrophilic macromolecule, a catalyst, and a label.

In some examples, the substrate includes a polymer disposed on a solid support. In some examples, the polymer is functionalized to include polyhedral oligomeric silsesquioxane (POSS).

In some examples, the method further includes providing a 4-substituted urazole including the oligonucleotide, and oxidizing the 4-substituted urazole to form the unsaturated cyclic dione triazolinedione including the oligonucleotide.

Some examples herein provide a composition that includes a substrate, and an adduct coupled to the substrate:

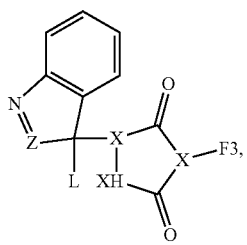

where L includes a linker to the substrate, F3 includes an oligonucleotide, each X independently is CH or N, and Z is CH or N.

In some examples, the adduct is:

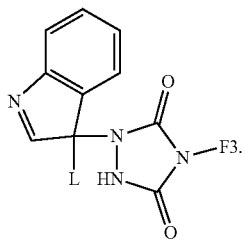

In some examples, the substrate includes a polymer disposed on a solid support. In some examples, the polymer is functionalized to include polyhedral oligomeric silsesquioxane (POSS).

Some examples herein provide a method of coupling a functional group to a substrate. The method may include providing a diene coupled to a substrate, and reacting the diene with an unsaturated cyclic dione including an oligonucleotide to form a first adduct coupling the oligonucleotide to the substrate.

In some examples, the unsaturated cyclic dione is:

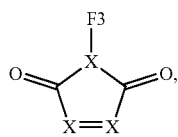

where F3 includes the oligonucleotide and each X independently is CH or N.

In some examples, the unsaturated cyclic dione is triazolinedione:

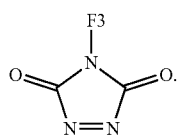

In some examples, the unsaturated cyclic dione is maleimide:

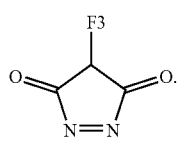

In some examples, the unsaturated cyclic dione is 4-cyclopentene-1,3-dione:

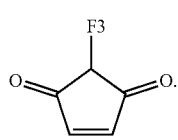

In some examples, the diene includes a 1,3-diene. In some examples, the 1,3-diene is:

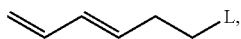

where L includes a linker to the substrate. In some examples, the adduct is:

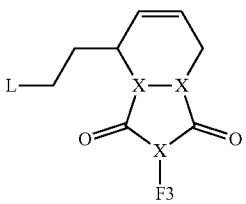

where L includes a linker to the substrate, each X independently is CH or N, and F3 includes the oligonucleotide.

In some examples, the adduct is:

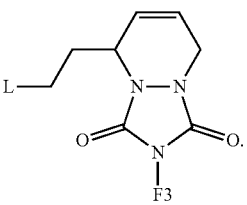

In some examples, the substrate includes a polymer disposed on a solid support. In some examples, the polymer is functionalized to include polyhedral oligomeric silsesquioxane (POSS).

In some examples, the method further includes providing a 4-substituted urazole including the oligonucleotide, and oxidizing the 4-substituted urazole to form the unsaturated cyclic dione triazolinedione including the oligonucleotide.

Some examples herein provide a composition that includes a substrate, and an adduct coupled to the substrate:

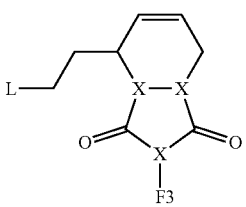

where L includes a linker to the substrate, each X independently is CH or N, and F3 is an oligonucleotide.

In some examples, the adduct is:

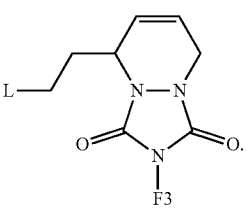

In some examples, the substrate includes a polymer disposed on a solid support. In some examples, the polymer is functionalized to include polyhedral oligomeric silsesquioxane (POSS).

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

DETAILED DESCRIPTION

Figure 1A:
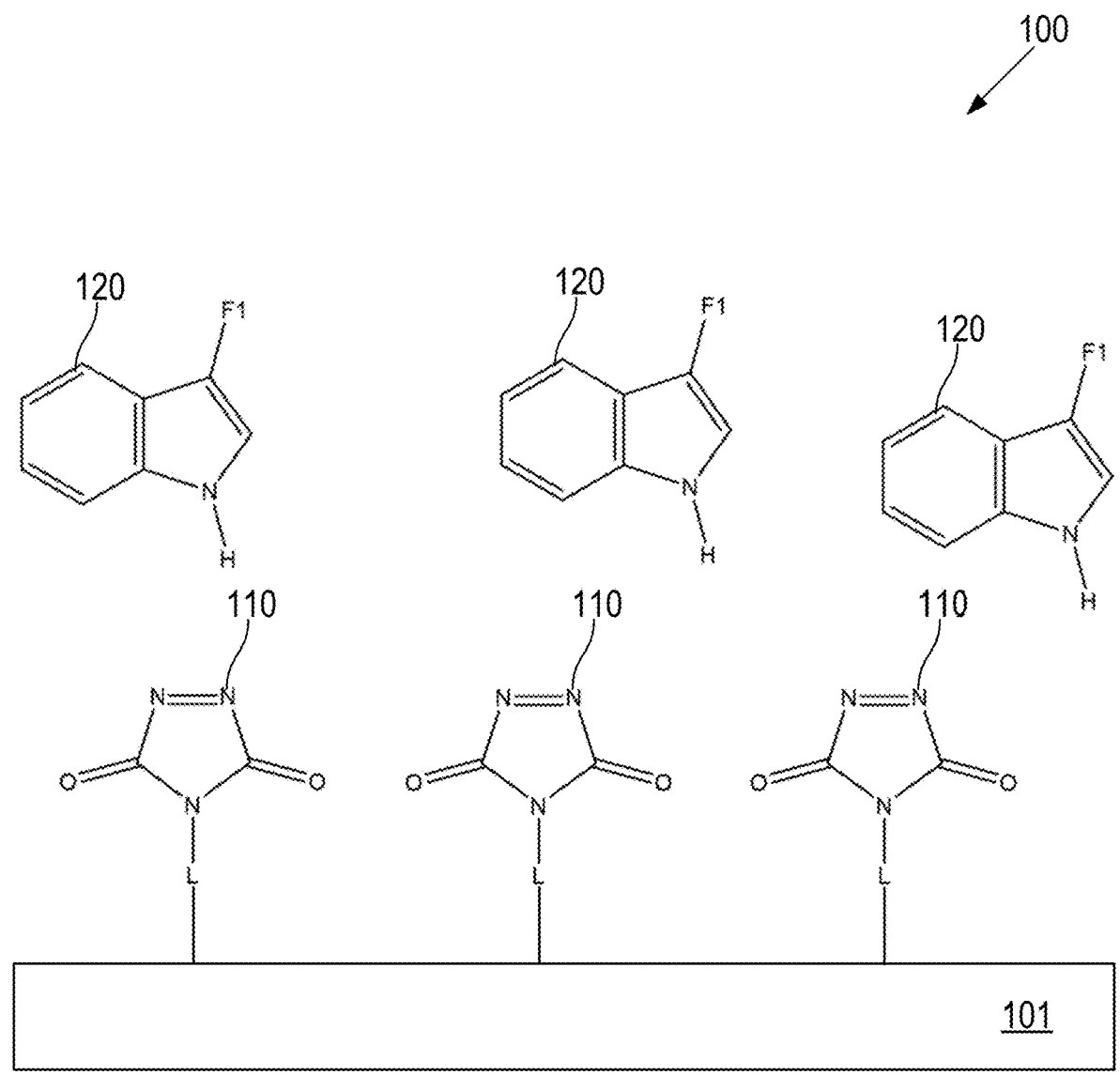
FIGS. 1A-1F schematically illustrate example compositions and operations in a process for coupling functional groups to a substrate.
Figure 1B:
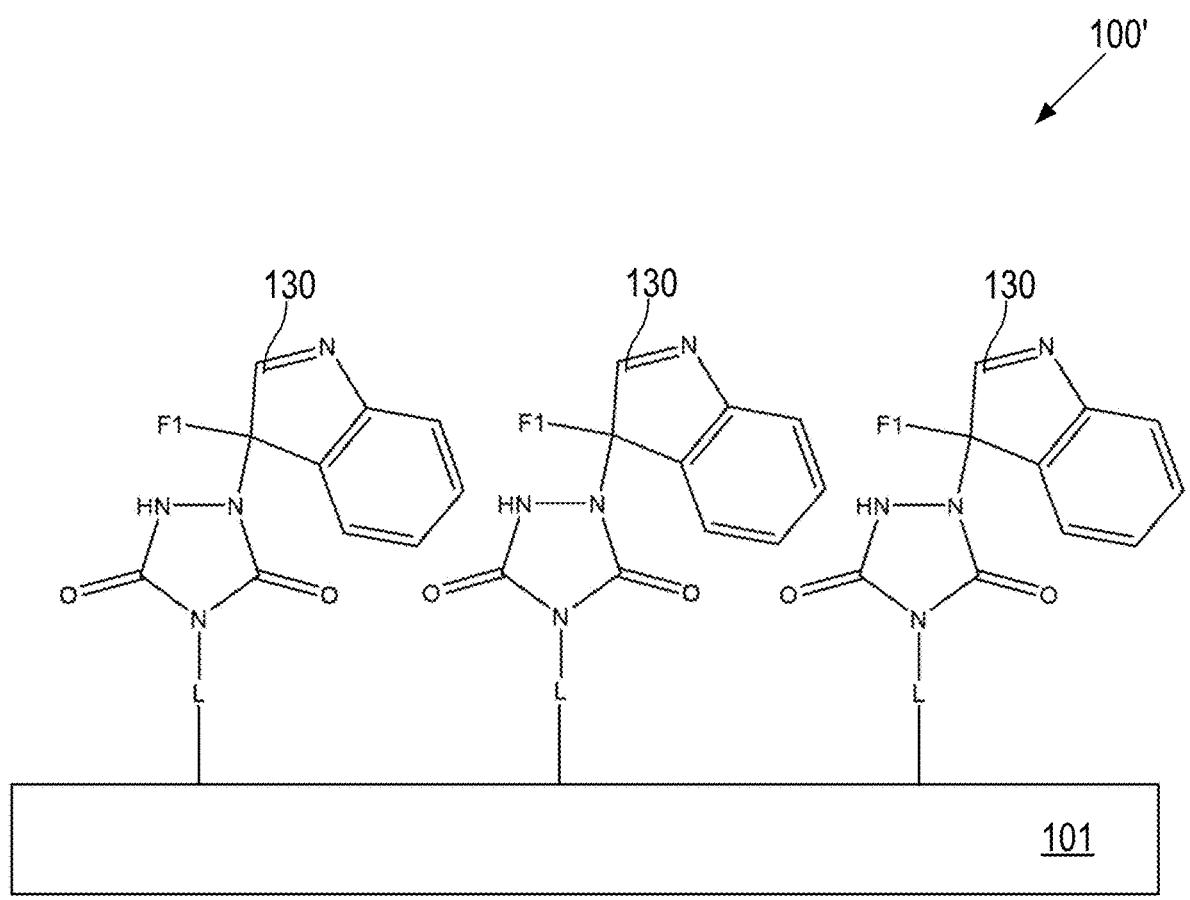
Figure 1C:
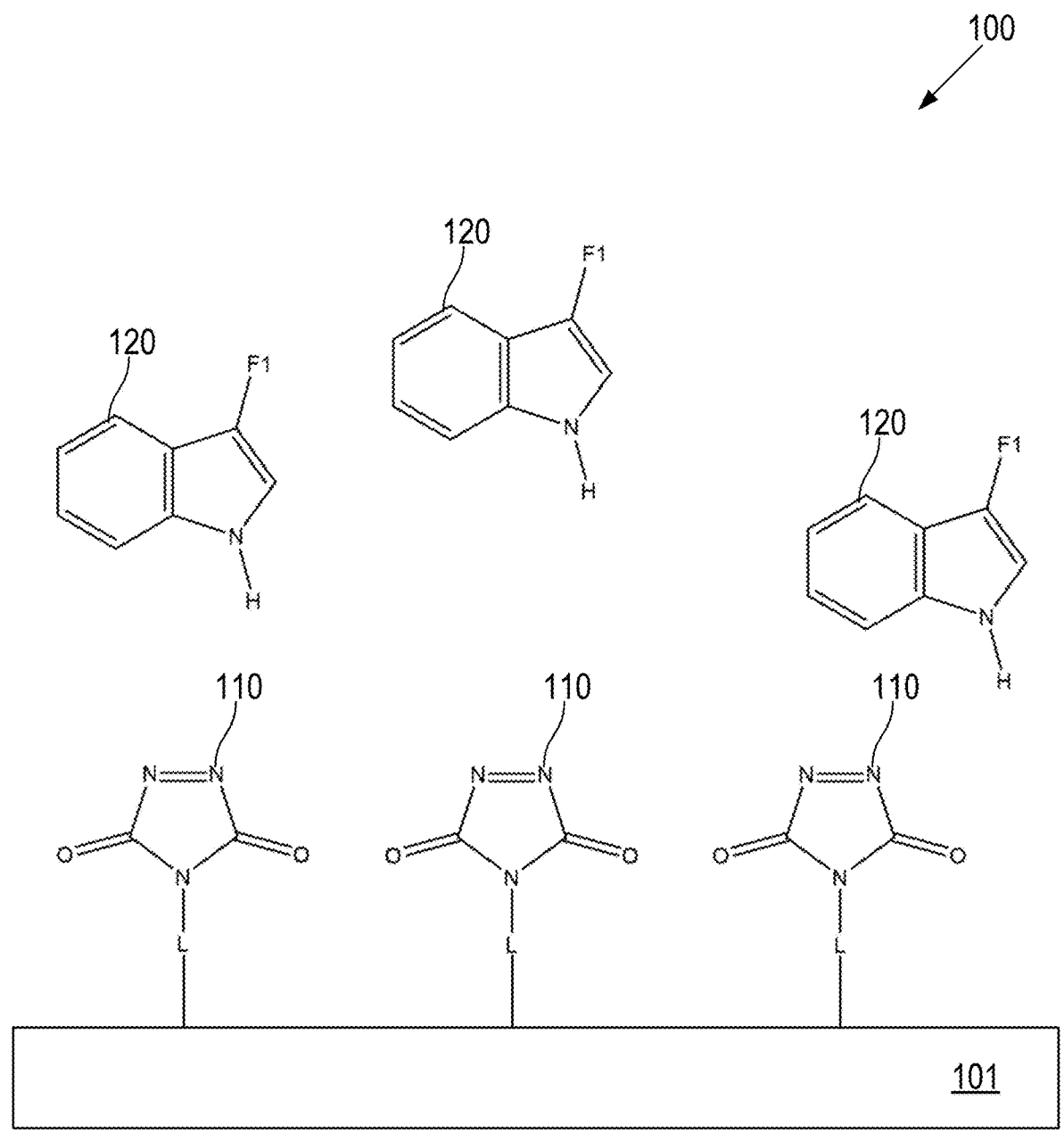

Examples provided herein are related to compositions including functional groups coupled to substrates, and methods of making the same. Methods of using such compositions also are disclosed.

For example, some previously known methods of coupling oligonucleotide primers to substrates may include the use of relatively harsh reagents such as cyanuric chloride, hydrazine, or diethyl ether to prepare the substrate. Additionally, some previously known coupling chemistry may utilize a hydrazone formation reaction between a hydrazine-functionalized glass substrate and an oligonucleotide bearing a 5'-aldehyde modification. As such, the chemistry may be performed at a relatively low pH of about 5, which may be problematic for oligonucleotide stability and may increase the likelihood of incurring nonspecific binding between the positively charged oligonucleotides and the glass substrate. Moreover, the hydrazone bond may be formed reversibly, and thus may increase the likelihood that the oligonucleotides may gradually decouple from the glass substrate. In some other previously known methods, oligonucleotide primers are coupled to polymeric substrates such as PAZAM using relatively harsh "Click chemistry" reagents such Cu(I) as well as a relatively high pH of around 7-11, which also may be problematic for oligonucleotide stability.

In comparison, provided herein is a method for preparing a functionalized surface that may accept one or more functional groups, such as but not limited to oligonucleotides, under approximately neutral or mildly basic pH conditions via one or more alternative "Click chemistry" reactions. The term "Click chemistry" refers to reactions that meet one or more criteria, e.g., may have relatively high yield, may be relatively wide in scope, may create byproducts that may be removed relatively easily, may be relatively simple to perform, may be conducted using relatively easily removable solvents and reagents, and/or may be conducted using relatively mild solvents and reagents. Additionally, or alternatively, "Click chemistry" reactions may be thermodynamically favored and may lead specifically to one product.

In some examples, functional groups may be coupled to substrates using reactions between unsaturated cyclic diones and dienes, indazoles, or indoles. In some specific examples provided herein, the unsaturated cyclic diones used in the present examples may be heterocyclic compounds that include an azo moiety connected to two carbonyl functionalities, e.g., may have a structure such as:

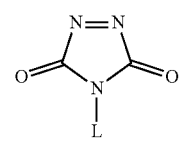

which may be referred to as triazoline dione (TAD), where L includes a linker to the substrate, and to which a functional group may be coupled using a diene or indole so as to couple that functional group to the substrate. The structure of the TAD molecule may stabilize the azo functionality through electronic conjugation. However, the electron-withdrawing carbonyls and the symmetry of the electronic system may result in orbital-controlled electrophilic reactivity, similar in certain respects to that of carbenes or singlet oxygen. As such, TAD molecules readily may participate in ultrafast Diels-Alder and ene-type reactions, and offer selective and predictable covalent linking reactions that have relatively high yields under equimolar conditions at relatively low temperature (e.g., at room temperature or below, e.g., at or below about 20° C.) within the need for a catalyst. TAD molecules show relatively high kinetic preference for electron-rich 7C systems, which allows for relatively good selectivity for indoles and for alternatively substituted dienes. Additionally, the adducts of reactions between TAD and indoles or dienes are robust heterocyclic scaffolds, compatible with a large number applications such as, but not limited to, those provided herein. As an additional feature, TAD molecules may be visually colorful while their reaction adducts with indoles or dienes may be colorless, providing an analytically accessible method of evaluating reaction efficiency. Other nonlimiting examples of unsaturated cyclic diones that may be used in the present compositions and methods are provided elsewhere herein.

In some examples, the surface-coupled TAD or other unsaturated cyclic dione is reacted with an indole having a structure such as:

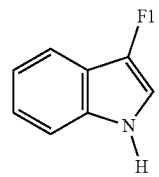

which may be referred to as 1H-indole, where F1 includes a functional group. In nonlimiting examples, such an indole may reversibly react with an unsaturated cyclic dione such as TAD in a "reversible Click" reaction, e.g., to form the adduct:

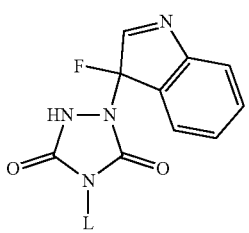

which may be referred to as a Michael-addition adduct of TAD and 1H-indole, and via which the functional group F1 is coupled to the substrate. Other nonlimiting examples of indoles and indazoles that may be reacted with other unsaturated cyclic diones are provided elsewhere herein.

In some examples, the surface-coupled TAD is reacted with a 1,3-diene having a structure such as:

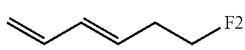

which may be referred to as trans,trans-1,3-hexadiene, where F2 includes a functional group. In some examples, such a diene may substantially irreversibly react with the unsaturated cyclic dione, such as TAD, in an "ultrafast Click" reaction, e.g., to form the adduct:

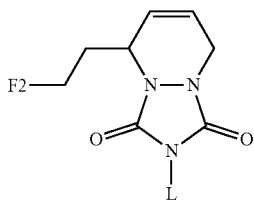

which may be referred to as a Diels-Alder cycloaddition product, and via which the functional group F2 is coupled to the substrate. Alternatively, the diene may substantially irreversibly react in a "transClick" reaction with the adduct of the "reversible Click" reaction between the TAD or other unsaturated cyclic dione and the indole or indazole, e.g., to form the adduct:

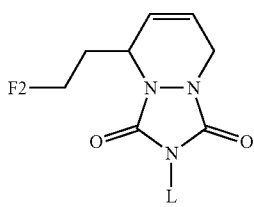

via which the functional group F2 is coupled to the substrate, and in which reaction the indole is displaced causing the functional group F1 to dissociate from the substrate.

Note that reactions such as described herein may be used to couple any suitable number and types of functional groups to the substrate at different times than one another. For example, the "reversible Click" reaction may be used to couple a first functional group (F1) to the substrate via the unsaturated cyclic dione (e.g., TAD) and indole or indazole, and the "transClick" reaction subsequently may be used to cause the first functional group to dissociate from the substrate via the indole or indazole and to couple a second functional group (F2) to the surface via the diene. Or, for example, because the "reversible Click" reaction is reversible, the unsaturated cyclic dione (e.g., TAD) coupled to the surface may be regenerated by heating the adduct of the "reversible Click" reaction to an appropriate temperature to cause dissociation of the indole or indazole. As such, the unsaturated cyclic dione (e.g., TAD) coupled to the surface then is available to react with another indole or indazole in another "reversible Click" reaction (which itself may be reversible) to couple another functional group to the substrate, or with a diene in an "ultrafast Click" reaction to couple yet another functional group to the substrate.

Although some examples may include the use of TAD or other unsaturated cyclic dione which is coupled to the substrate via a linker, it will be appreciated that in other examples, the unsaturated cyclic diones may be functionalized and may be coupled to the substrate via similar "reversible Click," "ultrafast Click," or "transClick" reactions. Illustratively, TAD have a structure such as:

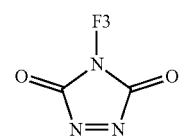

where F3 includes a functional group, and which may be coupled to the substrate via a diene, indole, or indazole that is coupled to the substrate. In some examples, the indole with which the solution-based TAD is reacted may have the structure:

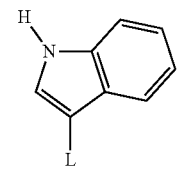

where L includes a linker to the substrate. The indole may react with the TAD in a reversible "reversible Click" reaction to form the adduct:

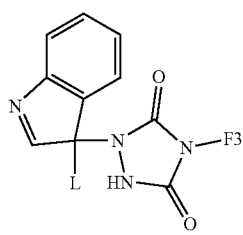

which is another Michael-addition adduct of TAD and 1H-indole, and via which the functional group F3 may be coupled to the substrate.

In some examples, the diene with which the solution-based TAD is reacted may be a 1,3-diene, which may have the structure:

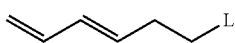

where L includes a linker to the substrate. The diene may react with the TAD or other unsaturated cyclic dione in a substantially irreversible "ultrafast Click" reaction, e.g., to form the adduct:

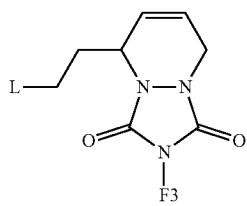

which is another Diels-Alder cycloaddition product, and via which the functional group F3 is coupled to the substrate.

Similarly as described above, because the "reversible Click" reaction is reversible, the surface-coupled indole or indazole may be regenerated by heating the adduct of the "reversible Click" reaction to an appropriate temperature to cause dissociation of the TAD, or other unsaturated cyclic dione, having the functional group attached thereto. As such, the indole or indazole then is available to react with another unsaturated cyclic dione (e.g., TAD) in another "reversible Click" reaction (which itself may be reversible) to couple another functional group to the substrate.

First, some terms used herein will be briefly explained. Then, some example compositions including functional groups coupled to a substrate, and example methods for making and using the same, will be described.

Terms

Unless defined otherwise, all technical and scientific terms used herein have the same meaning as is commonly understood by one of ordinary skill in the art. The use of the term "including" as well as other forms, such as "include," "includes," and "included," is not limiting. The use of the term "having" as well as other forms, such as "have," "has," and "had," is not limiting. As used in this specification, whether in a transitional phrase or in the body of the claim, the terms "comprise(s)" and "comprising" are to be interpreted as having an open-ended meaning. That is, the above terms are to be interpreted synonymously with the phrases "having at least" or "including at least." For example, when used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The terms "substantially", "approximately", and "about" used throughout this Specification are used to describe and account for small fluctuations, such as due to variations in processing. For example, they can refer to less than or equal to ±5%, such as less than or equal to ±2%, such as less than or equal to ±1%, such as less than or equal to ±0.5%, such as less than or equal to ±0.2%, such as less than or equal to ±0.1%, such as less than or equal to ±0.05%.

As used herein, the term "array" refers to a population of different molecules that are attached to one or more substrates such that the different molecules can be differentiated from each other according to relative location. An array can include different molecules that are each located at a different addressable location on a substrate. Alternatively or additionally, an array can include separate substrates each bearing a different molecule or molecules, wherein the different molecules can be identified according to the locations of the substrates on a surface to which the substrates are attached or according to the locations of the substrates in a liquid.

As used herein, the term "covalently attached" or "covalently bonded" refers to the forming of a chemical bonding that is characterized by the sharing of pairs of electrons between atoms. For example, a covalently attached molecule refers to a molecule that forms chemical bonds with a substrate, as compared to attachment to the surface via other means, for example, a non-covalent bond such as electrostatic interaction.

As used herein, "$C_a$ to $C_b$" or "$C_{a-b}$" in which "a" and "b" are integers refer to the number of carbon atoms in the specified group. That is, the group can contain from "a" to "b", inclusive, carbon atoms. Thus, for example, a "$C_1$ to $C_4$ alkyl" or "$C_{1-4}$ alkyl" or "$C_{1-4}$alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—.

The term "halogen" or "halo," as used herein, means fluorine, chlorine, bromine, or iodine, with fluorine and chlorine being examples.

As used herein, "alkyl" refers to a straight or branched hydrocarbon chain that is fully saturated (i.e., contains no double or triple bonds). The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 9 carbon atoms. The alkyl group could also be a lower alkyl having 1 to 4 carbon atoms. The alkyl group may be designated as "$C_{1-4}$ alkyl" or similar designations. By way of example only, "$C_{1-4}$ alkyl" or "$C_{1-4}$alkyl" indicates that there are one to four carbon atoms in the alkyl chain, i.e., the alkyl chain is selected from the group consisting of methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, hexyl, and the like.

As used herein, "alkenyl" refers to a straight or branched hydrocarbon chain containing one or more double bonds. The alkenyl group may have 2 to 20 carbon atoms, although the present definition also covers the occurrence of the term "alkenyl" where no numerical range is designated. The alkenyl group may also be a medium size alkenyl having 2 to 9 carbon atoms. The alkenyl group could also be a lower alkenyl having 2 to 4 carbon atoms. The alkenyl group may be designated as "$C_{2-4}$ alkenyl" or similar designations. By way of example only, "$C_{2-4}$ alkenyl" indicates that there are two to four carbon atoms in the alkenyl chain, i.e., the alkenyl chain is selected from the group consisting of ethenyl, propen-1-yl, propen-2-yl, propen-3-yl, buten-1-yl, buten-2-yl, buten-3-yl, buten-4-yl, 1-methyl-propen-1-yl, 2-methyl-propen-1-yl, 1-ethyl-ethen-1-yl, 2-methyl-propen-3-yl, buta-1,3-dienyl, buta-1,2,-dienyl, and buta-1,2-dien-4- yl. Typical alkenyl groups include, but are in no way limited to, ethenyl, propenyl, butenyl, pentenyl, and hexenyl, and the like.

Groups that include an alkenyl group include optionally substituted alkenyl, cycloalkenyl, and heterocycloalkenyl groups.

As used herein, "alkynyl" refers to a straight or branched hydrocarbon chain containing one or more triple bonds. The alkynyl group may have 2 to 20 carbon atoms, although the present definition also covers the occurrence of the term "alkynyl" where no numerical range is designated. The alkynyl group may also be a medium size alkynyl having 2 to 9 carbon atoms. The alkynyl group could also be a lower alkynyl having 2 to 4 carbon atoms. The alkynyl group may be designated as "$C_{2-4}$ alkynyl" or similar designations. By way of example only, "$C_{2-4}$ alkynyl" or "$C_{2-4}$alkynyl" indicates that there are two to four carbon atoms in the alkynyl chain, i.e., the alkynyl chain is selected from the group consisting of ethynyl, propyn-1-yl, propyn-2-yl, butyn-1-yl, butyn-3-yl, butyn-4-yl, and 2-butynyl. Typical alkynyl groups include, but are in no way limited to, ethynyl, propynyl, butynyl, pentynyl, and hexynyl, and the like.

Groups that include an alkynyl group include optionally substituted alkynyl, cycloalkynyl, and heterocycloalkynyl groups.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms, although the present definition also covers the occurrence of the term "aryl" where no numerical range is designated. In some examples, the aryl group has 6 to 10 carbon atoms.

The aryl group may be designated as "$C_{6-10}$ aryl," "$C_6$ or $C_{10}$ aryl," or similar designations. Examples of aryl groups include, but are not limited to, phenyl, naphthyl, azulenyl, and anthracenyl.

As used herein, "heterocycle" refers to a cyclic compound which includes atoms of carbon along with another atom (heteroatom), for example nitrogen, oxygen or sulfur.

Heterocycles may be aromatic (heteroaryl) or aliphatic. An aliphatic heterocycle may be completely saturated or may contain one or more or two or more double bonds, for example the heterocycle may be a heterocycloalkyl. The heterocycle may include a single heterocyclic ring or multiple heterocyclic rings that are fused.

As used herein, "heteroaryl" refers to an aromatic ring or ring system (i.e., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members (i.e., the number of atoms making up the ring backbone, including carbon atoms and heteroatoms), although the present definition also covers the occurrence of the term "heteroaryl" where no numerical range is designated. In some examples, the heteroaryl group has 5 to 10 ring members or 5 to 7 ring members. The heteroaryl group may be designated as "5-7 membered heteroaryl," "5-10 membered heteroaryl," or similar designations. Examples of heteroaryl rings include, but are not limited to, furyl, thienyl, phthalazinyl, pyrrolyl, oxazolyl, thiazolyl, imidazolyl, pyrazolyl, isoxazolyl, isothiazolyl, triazolyl, thiadiazolyl, pyridinyl, pyridazinyl, pyrimidinyl, pyrazinyl, triazinyl, quinolinyl, isoquinlinyl, benzimidazolyl, benzoxazolyl, benzothiazolyl, indolyl, isoindolyl, and benzothienyl.

As used herein, "cycloalkyl" means a fully saturated carbocyclyl ring or ring system. Examples include cyclopropyl, cyclobutyl, cyclopentyl, and cyclohexyl.

As used herein, "cycloalkenyl" or "cycloalkene" means a carbocyclyl ring or ring system having at least one double bond, wherein no ring in the ring system is aromatic. An example is cyclohexenyl or cyclohexene. Another example is norbornene or norbornenyl.

As used herein, "heterocycloalkenyl" or "heterocycloalkene" means a carbocyclyl ring or ring system with at least one heteroatom in ring backbone, having at least one double bond, wherein no ring in the ring system is aromatic. In some examples, heterocycloalkenyl or heterocycloalkene ring or ring system is 3-membered, 4-membered, 5-membered, 6-membered, 7-membered, 8-membered, 9-membered, or 10-membered.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Another example is dibenzocyclooctyne (DBCO).

As used herein, "heterocycloalkynyl" or "heterocycloalkyne" means a carbocyclyl ring or ring system with at least one heteroatom in ring backbone, having at least one triple bond, wherein no ring in the ring system is aromatic. In some examples, heterocycloalkynyl or heterocycloalkyne ring or ring system is 3-membered, 4-membered, 5-membered, 6-membered, 7-membered, 8-membered, 9-membered, or 10-membered.

As used herein, "heterocycloalkyl" means a non-aromatic cyclic ring or ring system containing at least one heteroatom in the ring backbone. Heterocycloalkyls may be joined together in a fused, bridged or spiro-connected fashion. Heterocycloalkyls may have any degree of saturation provided that at least one heterocyclic ring in the ring system is not aromatic. The heterocycloalkyl group may have 3 to 20 ring members (i.e., the number of atoms making up the ring backbone, including carbon atoms and heteroatoms), although the present definition also covers the occurrence of the term "heterocycloalkyl" where no numerical range is designated. The heterocycloalkyl group may also be a medium size heterocycloalkyl having 3 to 10 ring members. The heterocycloalkyl group could also be a heterocycloalkyl having 3 to 6 ring members. The heterocycloalkyl group may be designated as "3-6 membered heterocycloalkyl" or similar designations. In some six membered monocyclic heterocycloalkyls, the heteroatom(s) are selected from one up to three of O, N or S, and in some five membered monocyclic heterocycloalkyls, the heteroatom(s) are selected from one or two heteroatoms selected from O. N, or S. Examples of heterocycloalkyl rings include, but are not limited to, azepinyl, acridinyl, carbazolyl, cinnolinyl, dioxolanyl, imidazolinyl, imidazolidinyl, morpholinyl, oxiranyl, oxepanyl, thiepanyl, piperidinyl, piperazinyl, dioxopiperazinyl, pyrrolidinyl, pyrrolidonyl, pyrrolidionyl, 4-piperidonyl, pyrazolinyl, pyrazolidinyl, 1,3-dioxinyl, 1,3-dioxanyl, 1,4-dioxinyl, 1,4-dioxanyl, 1,3-oxathianyl, 1,4-oxathiinyl, 1,4-oxathianyl, 2H-1,2-oxazinyl, trioxanyl, hexahydro-1,3,5-triazinyl, 1,3-dioxolyl, 1,3-dioxolanyl, 1,3-dithiolyl, 1,3-dithiolanyl, isoxazolinyl, isoxazolidinyl, oxazolinyl, oxazolidinyl, oxazolidinonyl, thiazolinyl, thiazolidinyl, 1,3-oxathiolanyl, indolinyl, isoindolinyl, tetrahydrofuranyl, tetrahydropyranyl, tetrahydrothiophenyl, tetrahydrothiopyranyl, tetrahydro-1,4-thiazinyl, thiamorpholinyl, dihydrobenzofuranyl, benzimidazolidinyl, and tetrahydroquinoline.

As used herein, a substituted group is derived from the unsubstituted parent group in which there has been an exchange of one or more hydrogen atoms for another atom or group.

Unless otherwise indicated, when a group is deemed to be "substituted," it is meant that the group is substituted with one or more substituents independently selected from $C_1$-$C_6$ alkyl, $C_1$-$C_6$ alkenyl, $C_1$-$C_6$ alkynyl, $C_1$-$C_6$ heteroalkyl, $C_3$-$C_7$ carbocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), $C_3$-$C_7$-carbocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heterocyclyl-$C_1$-$C_6$-alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl (optionally substituted with halo, $C_1$-$C_6$ alkyl, $C_1$-$C_6$ alkoxy, $C_1$-$C_6$ haloalkyl, and $C_1$-$C_6$ haloalkoxy), aryl($C_1$-$C_6$)alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl (optionally substituted with halo, $C_1$-$C_6$ alkyl, $C_1$-$C_6$ alkoxy, $C_1$-$C_6$ haloalkyl, and $C_1$-$C_6$ haloalkoxy), 5-10 membered heteroaryl($C_1$-$C_6$) alkyl (optionally substituted with halo, $C_1$-$C_6$ alkyl, $C_1$-$C_6$ alkoxy, $C_1$-$C_6$ haloalkyl, and $C_1$-$C_6$ haloalkoxy), halo, cyano, hydroxy, $C_1$-$C_6$ alkoxy, $C_1$-$C_6$ alkoxy($C_1$-$C_6$)alkyl (i.e., ether), aryloxy, sulfhydryl (mercapto), halo($C_1$-$C_6$) alkyl (e.g., —$CF_3$), halo($C_1$-$C_6$)alkoxy (e.g., —$OCF_3$), $C_1$-$C_6$ alkylthio, arylthio, amino, amino($C_1$-$C_6$)alkyl, nitro, O-carbamyl, N-carbamyl, O-thiocarbamyl, N-thiocarbamyl, C-amido, N-amido, S-sulfonamido, N-sulfonamido, C-carboxy, O-carboxy, acyl, cyanato, isocyanato, thiocyanato, isothiocyanato, sulfinyl, sulfonyl, and oxo (=O). Wherever a group is described as "optionally substituted" that group can be substituted with the above substituents.

Where the compounds disclosed herein have at least one stereocenter, they may exist as individual enantiomers or diastereomers, or as mixtures of such isomers, including racemates. Separation of the individual isomers or selective synthesis of the individual isomers is accomplished by application of various methods which are well known to practitioners in the art. Where compounds disclosed herein are understood to exist in tautomeric forms, all tautomeric forms are included in the scope of the structures depicted. Unless otherwise indicated, all such isomers and mixtures thereof are included in the scope of the compounds disclosed herein. Furthermore, compounds disclosed herein may exist in one or more crystalline or amorphous forms. Unless otherwise indicated, all such forms are included in the scope of the compounds disclosed herein including any polymorphic forms. In addition, some of the compounds disclosed herein may form solvates with water (i.e., hydrates) or common organic solvents.

Unless otherwise indicated, such solvates are included in the scope of the compounds disclosed herein.

As used herein, the term "nucleotide" is intended to mean a molecule that includes a sugar and at least one phosphate group, and in some examples also includes a nucleobase. A nucleotide that lacks a nucleobase may be referred to as "abasic." Nucleotides include deoxyribonucleotides, modified deoxyribonucleotides, ribonucleotides, modified ribonucleotides, peptide nucleotides, modified peptide nucleotides, modified phosphate sugar backbone nucleotides, and mixtures thereof. Examples of nucleotides include adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP), and deoxyuridine triphosphate (dUTP).

As used herein, the term "nucleotide" also is intended to encompass any nucleotide analogue which is a type of nucleotide that includes a modified nucleobase, sugar and/or phosphate moiety compared to naturally occurring nucleotides. Example modified nucleobases include inosine, xathanine, hypoxathanine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thiouracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. As is known in the art, certain nucleotide analogues cannot become incorporated into a polynucleotide, for example, nucleotide analogues such as adenosine 5'-phosphosulfate. Nucleotides may include any suitable number of phosphates, e.g., three, four, five, six, or more than six phosphates.

As used herein, the term "polynucleotide" refers to a molecule that includes a sequence of nucleotides that are bonded to one another, and may be used interchangeably with the term "oligonucleotide." The terms "polynucleotide" and "oligonucleotide" are used interchangeably herein. The different terms are not intended to denote any particular difference in size, sequence, or other property unless specifically indicated otherwise. For clarity of description the terms may be used to distinguish one species of polynucleotide from another when describing a particular method or composition that includes several polynucleotide species. A polynucleotide is one nonlimiting example of a polymer. Examples of polynucleotides include deoxyribonucleic acid (DNA), ribonucleic acid (RNA), locked nucleic acid (LNA), peptide nucleic acid (PNA), and analogues thereof. A polynucleotide may be a single stranded sequence of nucleotides, such as RNA or single stranded DNA, a double stranded sequence of nucleotides, such as double stranded DNA, or may include a mixture of a single stranded and double stranded sequences of nucleotides. Double stranded DNA (dsDNA) includes genomic DNA, and PCR and amplification products. Single stranded DNA (ssDNA) can be converted to dsDNA and vice-versa. Polynucleotides may include non-naturally occurring DNA, such as enantiomeric DNA. The precise sequence of nucleotides in a polynucleotide may be known or unknown. The following are examples of polynucleotides: a gene or gene fragment (for example, a probe, primer, expressed sequence tag (EST) or serial analysis of gene expression (SAGE) tag), genomic DNA, genomic DNA fragment, exon, intron, messenger RNA (mRNA), transfer RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the foregoing.

As used herein, a "polymerase" is intended to mean an enzyme having an active site that assembles polynucleotides by polymerizing nucleotides into polynucleotides. A polymerase can bind a primed single stranded target polynucleotide, and can sequentially add nucleotides to the growing primer to form a "complementary copy" polynucleotide having a sequence that is complementary to that of the target polynucleotide. Another polymerase, or the same polymerase, then can form a copy of the target nucleotide by forming a complementary copy of that complementary copy polynucleotide. Any of such copies may be referred to herein as "amplicons." DNA polymerases may bind to the target polynucleotide and then move down the target polynucleotide sequentially adding nucleotides to the free hydroxyl group at the 3' end of a growing polynucleotide strand (growing amplicon). DNA polymerases may synthesize complementary DNA molecules from DNA templates and RNA polymerases may synthesize RNA molecules from DNA templates (transcription). Polymerases may use a short RNA or DNA strand (primer), to begin strand growth. Some polymerases may displace the strand upstream of the site where they are adding bases to a chain. Such polymerases may be said to be strand displacing, meaning they have an activity that removes a complementary strand from a template strand being read by the polymerase. Example polymerases having strand displacing activity include, without limitation, the large fragment of Bst (Bacillus stearothermophilus) polymerase, exo-Klenow polymerase or sequencing grade T7 exo-polymerase. Some polymerases degrade the strand in front of them, effectively replacing it with the growing chain behind (5' exonuclease activity). Some polymerases have an activity that degrades the strand behind them (3' exonuclease activity). Some useful polymerases have been modified, either by mutation or otherwise, to reduce or eliminate 3' and/or 5' exonuclease activity.

As used herein, the term "primer" refers to a polynucleotide to which nucleotides may be added via a free 3' OH group. The primer length may be any suitable number of bases long and may include any suitable combination of natural and non-natural nucleotides. A target polynucleotide may include an "adapter" that hybridizes to (has a sequence that is complementary to) a primer, and may be amplified so as to generate a complementary copy polynucleotide by adding nucleotides to the free 3' OH group of the primer. A primer may be coupled to a substrate.

In some examples, the primers used on the substrate surface are P5 and P7 primers that are commercially available from Illumina, Inc. The P5 and P7 primer sequences may have the following sequences, in some examples:

Paired Read Set

P5:
(SEQ ID NO: 1)
5'-AATGATACGGCGACCACCGAGAUCTACAC-3'

P7:
(SEQ ID NO: 2)
5'-CAAGCAGAAGACGGCATACGAG*AT-3'

Single Read Set

P5:
(SEQ ID NO: 3)
5'-AATGATACGGCGACCACCGA-3'

P7:
(SEQ ID NO: 4)
5'-CAAGCAGAAGACGGCATACGA-3' where G* is G or 8-oxoguanine.

In some examples, the attached oligonucleotides (such as primers or P5 or P7 primers) include a linker or spacer at the 5' end. Such linker or spacer may be included in order to permit chemical or enzymatic cleavage, or to confer some other desirable property, for example to enable covalent attachment to a polymer or a solid support, or to act as spacers to position the site of cleavage an optimal distance from the solid support. In certain cases, 10 spacer nucleotides may be positioned between the point of attachment of the P5 or P7 primers to a polymer or a solid support. In some examples, polyT spacers are used, although other nucleotides and combinations thereof can also be used. In one example, the spacer is a 6T to 10T spacer. In some examples, the linkers include cleavable nucleotides including a chemically cleavable functional group such as a vicinal diol or allyl T.

As used herein, the term "amplicon," when used in reference to a polynucleotide, is intended to mean a product of copying the polynucleotide, wherein the product has a nucleotide sequence that is substantially the same as, or is substantially complementary to, at least a portion of the nucleotide sequence of the polynucleotide. "Amplification" and "amplifying" refer to the process of making an amplicon of a polynucleotide. A first amplicon of a target polynucleotide may be a complementary copy. Additional amplicons are copies that are created, after generation of the first amplicon, from the target polynucleotide or from the first amplicon. A subsequent amplicon may have a sequence that is substantially complementary to the target polynucleotide or is substantially identical to the target polynucleotide. It will be understood that a small number of mutations (e.g., due to amplification artifacts) of a polynucleotide may occur when generating an amplicon of that polynucleotide.

As used herein, the term "silane" refers to an organic or inorganic compound containing one or more silicon atoms. A non-limiting example of an inorganic silane compound is SiH4, or halogenated SiH4 where hydrogen is replaced by one or more halogen atoms. A non-limiting example of an organic silane compound is $X-R^C-Si(OR^D)_3$, wherein X is a non-hydrolyzable organic group, such as amino, vinyl, epoxy, methacrylate, sulfur, alkyl, alkenyl, or alkynyl; $R^C$ is a spacer, for example $-(CH_2)_n-$, wherein n is 0 to 1000; each $R^D$ is independently selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. In some examples, the silanes may be cross-linked such that the oxygen atom of an $-OR^D$ group of $X-R^C-Si(OR^D)_3$, is attached to the silicon atom of an adjacent organic silane compound, X—$R^C$—Si(O$R^D$)$_3$. Furthermore, the silane compounds may be attached to a substrate surface by covalent binding of the X—$R^C$—Si(O$R^D$)$_3$ moieties to oxygen atoms on the surface. Thus, in some examples, the silanes described include the following structure:

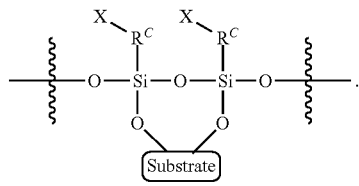

As used herein, the term "silane" can include mixtures of different silane compounds. In some examples, X is a norbornenyl group. In some examples, X is a bicyclononynyl group. In some examples, X is an alkene- or alkyne-containing group. In some examples, X is alkene or alkyne. In some examples, the $R^C$ linker is a $C_{2-6}$ alkylene group.

As used herein, the term "substrate" refers to a material that includes a solid support. A substrate may include a polymer that defines the solid support, or that is disposed on the solid support. Example substrate materials may include glass, silica, plastic, quartz, metal, metal oxide, organo-silicate (e.g., polyhedral organic silsesquioxanes (POSS)), polyacrylates, tantalum oxide, complementary metal oxide semiconductor (CMOS), or combinations thereof. An example of POSS can be that described in Kehagias et al., Microelectronic Engineering 86 (2009), pp. 776-778, which is incorporated by reference in its entirety. Illustratively, POSS-containing monomers may be polymerised reaching a gel-point rapidly to furnish a POSS resin (a polymer functionalized to include POSS) on which soft material functionalisation may be performed. In some examples, substrates used in the present application include silica-based substrates, such as glass, fused silica, or other silica-containing material. In some examples, substrates may include silicon, silicon nitride, or silicone hydride. In some examples, substrates used in the present application include plastic materials or components such as polyethylene, polystyrene, poly(vinyl chloride), polypropylene, nylons, polyesters, polycarbonates, and poly(methyl methacrylate). Example plastics materials include poly(methyl methacrylate), polystyrene, and cyclic olefin polymer substrates. In some examples, the substrate is or includes a silica-based material or plastic material or a combination thereof In particular examples, the substrate has at least one surface comprising glass or a silicon-based polymer. In some examples, the substrates may include a metal. In some such examples, the metal is gold. In some examples, the substrate has at least one surface comprising a metal oxide. In one example, the surface comprises a tantalum oxide or tin oxide. Acrylamides, enones, or acrylates may also be utilized as a substrate material or component. Other substrate materials may include, but are not limited to gallium arsenide, indium phosphide, aluminum, ceramics, polyimide, quartz, resins, polymers and copolymers. In some examples, the substrate and/or the substrate surface may be, or include, quartz. In some other examples, the substrate and/or the substrate surface may be, or include, semiconductor, such as GaAs or ITO. The foregoing lists are intended to be illustrative, but not limiting to the present application. Substrates may comprise a single material or a plurality of different materials. Substrates may be composites or laminates. In some examples, the substrate comprises an organo-silicate material. Substrates may be flat, round, spherical, rod-shaped, or any other suitable shape. Substrates may be rigid or flexible. In some examples, a substrate is a bead or a flow cell.

In some examples, a substrate includes a patterned surface. A "patterned surface" refers to an arrangement of different regions in or on an exposed layer of a substrate. For example, one or more of the regions may be features where one or more capture primers are present. The features can be separated by interstitial regions where capture primers are not present. In some examples, the pattern may be an x-y format of features that are in rows and columns. In some examples, the pattern may be a repeating arrangement of features and/or interstitial regions. In some examples, the pattern may be a random arrangement of features and/or interstitial regions. In some examples, the substrate includes an array of wells (depressions) in a surface. The wells may be provided by substantially vertical sidewalls. In some examples, the substrate includes an array of posts (protrusions) in a surface. Wells and posts may be fabricated as is generally known in the art using a variety of techniques, including, but not limited to, photolithography, stamping techniques, molding techniques, nano-imprint lithography, and microetching techniques. As will be appreciated by those in the art, the technique used will depend on the composition and shape of the array substrate. Illustratively, posts having diameters between about 50 nm to about 500 nm may be referred to as nanoposts, and may have heights of similar dimension to the diameters.

The features in a patterned surface of a substrate may include an array of features (e.g., wells such as microwells or nanowells, or posts such as nanoposts) on glass, silicon, plastic or other suitable material(s) with patterned, covalently-linked gel such as poly(N-(5-azidoacetamidylpentyl) acrylamide-co-acrylamide) (PAZAM). The process creates gel pads used for sequencing that may be stable over sequencing runs with a large number of cycles. The covalent linking of the polymer to the wells may be helpful for maintaining the gel in the structured features throughout the lifetime of the structured substrate during a variety of uses. However in many examples, the gel need not be covalently linked to the wells. For example, in some conditions silane free acrylamide (SFA) which is not covalently attached to any part of the structured substrate, may be used as the gel material.

In particular examples, a structured substrate may be made by patterning a suitable material with wells (e.g. microwells or nanowells), coating the patterned material with a gel material (e.g., PAZAM, SFA or chemically modified variants thereof, such as the azidolyzed version of SFA (azido-SFA)) and polishing the surface of the gel coated material, for example via chemical or mechanical polishing, thereby retaining gel in the wells but removing or inactivating substantially all of the gel from the interstitial regions on the surface of the structured substrate between the wells. Primers may be attached to gel material. A solution including a plurality of target polynucleotides (e.g., a fragmented human genome or portion thereof) may then be contacted with the polished substrate such that individual target polynucleotides will seed individual wells via interactions with primers attached to the gel material; however, the target polynucleotides will not occupy the interstitial regions due to absence or inactivity of the gel material. Amplification of the target polynucleotides may be confined to the wells because absence or inactivity of gel in the interstitial regions may inhibit outward migration of the growing cluster. The process is conveniently manufacturable, being scalable and utilizing conventional micro- or nano-fabrication methods.

A patterned substrate may include, for example, wells etched provided in a slide or chip. The pattern of the etchings and geometry of the wells may take on a variety of different shapes and sizes, and such features may be physically or functionally separable from each other. Particularly useful substrates having such structural features include patterned substrates that may select the size of solid particles such as microspheres. An example patterned substrate having these characteristics is the etched substrate used in connection with BEAD ARRAY technology (Illumina, Inc., San Diego, Calif.). Nano-imprint lithography (NIL) may be used to provide wells.

In some examples, a substrate described herein forms at least part of a flow cell or is located in or coupled to a flow cell. Flow cells may include a flow chamber that is divided into a plurality of lanes or a plurality of sectors. Example flow cells and substrates for manufacture of flow cells that may be used in methods and compositions set forth herein include, but are not limited to, those commercially available from Illumina, Inc. (San Diego, CA).

As used herein, the term "structure" refers to a compound, for example a copolymer, that is bonded to a substrate. The copolymer may for example be covalently bonded to the substrate, for example via an azido group.

As used herein, the term "polymer" refers to a molecule including many repeated subunits or recurring units. Non-limiting examples of polymer structures include linear, branched, or hyper-branched polymers. Non-limiting examples of linear polymers including block copolymers or random/statistical copolymers. Non-limiting examples of branched polymers include star polymers, star-shaped or star-block polymers including both hydrophobic and hydrophilic segments, H-shaped polymers including both hydrophobic and hydrophilic segments, dumbbell shaped polymers, comb polymers, brush polymers, dendronized polymers, ladders, and dendrimers. Polymers may be cross-linked, or lightly cross-linked. Polymers as described herein may be linear, branched, hyper-branched or dendritic. The polymers described herein can also be in the form of polymer nanoparticles. Other examples of polymer architectures include, but not limited to ring block polymers and coil-cycle-coil polymers.

Polymers with more than one type of recurring unit can be arranged as block copolymers, random copolymers, or alternating copolymers, or mixtures thereof. The final copolymer structure can be in different architectures, including, for example, random copolymer, block copolymer, comb-shaped polymer or star-shaped polymer architectures. Different classes of polymer backbones include, but are not limited to, polyacrylamides, polyacrylates, polyurethanes, polysiloxanes, silicones, polyacroleins, polyphosphazenes, polyisocyanates, poly-ols, polysaccharides, polypeptides, and combinations thereof In some examples, the polymer includes polyacrylamide backbone. In some other examples, the polymer includes polyacrylate backbone. In still some other examples, the polymer includes polyurethane backbone. In still some other examples, the polymer includes polyphosphazene backbone. In still some other examples, the polymer includes a dendrimer backbone.

As used herein, the term "fluorophore" is intended to mean a molecule that emits light at a first wavelength responsive to excitation with light at a second wavelength that is different from the first wavelength. The light emitted by a fluorophore may be referred to as "fluorescence" and may be detected by suitable optical circuitry.

As used herein, to "detect" fluorescence is intended to mean to receive light from a fluorophore, to generate an electrical signal based on the received light, and to determine, using the electrical signal, that light was received from the fluorophore. Fluorescence may be detected using any suitable optical detection circuitry, which may include an optical detector to generate an electrical signal based on the light received from the fluorophore, and electronic circuitry to determine, using the electrical signal, that light was received from the fluorophore. As one example, the optical detector may include an active-pixel sensor (APS) including an array of amplified photodetectors configured to generate an electrical signal based on light received by the photodetectors. APSs may be based on complementary metal oxide semiconductor (CMOS) technology known in the art. CMOS-based detectors may include field effect transistors (FETs), e.g., metal oxide semiconductor field effect transistors (MOSFETs). In particular examples, a CMOS imager having a single-photon avalanche diode (CMOS-SPAD) may be used, for example, to perform fluorescence lifetime imaging (FLIM). In other examples, the optical detector may include a photodiode, such as an avalanche photodiode, charge-coupled device (CCD), cryogenic photon detector, reverse-biased light emitting diode (LED), photoresistor, phototransistor, photovoltaic cell, photomultiplier tube (PMT), quantum dot photoconductor or photodiode, or the like. The optical detection circuitry further may include any suitable combination of hardware and software in operable communication with the optical detector so as to receive the electrical signal therefrom, and configured to detect the fluorescence based on such signal, e.g., based on the optical detector detecting light from the fluorophore. For example, the electronic circuitry may include a memory and a processor coupled to the memory. The memory may store instructions for causing the processor to receive the signal from the optical detector and to detect the fluorophore using such signal. For example, the instructions can cause the processor to determine, using the signal from the optical detector, that fluorescence is emitted within the field of view of the optical detector and to determine, using such determination, that a fluorophore is present.

As used herein, the term "adduct" is intended to mean the product of a chemical reaction between two or more molecules, where the product contains all of the atoms of the molecules that were reacted.

As used herein, the term "linker" is intended to mean a molecule or molecules via which one element is attached to another element. For example, a linker may attach a molecule to a substrate. Linkers may be covalent, or may be non-covalent. Nonlimiting examples of covalent linkers include alkyl chains, polyethers, amides, esters, aryl groups, polyaryls, and the like. Nonlimiting examples of noncovalent linkers include host-guest complexation, cyclodextrin/norbornene, adamantane inclusion complexation with (3-CD, DNA hybridization interactions, and the like.

As used herein, the term "functional group" is intended to mean a molecule or molecules that may interact with one or more other molecules. As used herein, an element that is referred to as "functionalized" means that the element includes a functional group. For example, a functional group may covalently bond to one or more other molecules, e.g., may reversibly or substantially irreversibly react with one or more other molecules to form a product. Or, for example, a functional group may noncovalently associate with one or more other molecules. Nonlimiting examples of functional groups include oligonucleotides, hydrophilic molecule, hydrophilic macromolecule, a catalyst, and a label. Illustratively, a functional group including an oligonucleotide (such as a primer) may hybridize with another oligonucleotide (such as a polynucleotide to be amplified or sequenced). Or, a functional group including a label may include a fluorophore or FRET (Förster resonance energy transfer) partner, and detection of fluorescence from the fluorophore or FRET partner may be used to characterize the molecule to which the label is attached.

Compositions Including Functional Groups Coupled to Substrates, and Methods of Making the Same As noted above and as described in greater detail below, the present compositions and methods provide a facile way to couple any suitable functional groups to a substrate, and in some examples to sequentially couple different functional groups to the substrate using common reaction components. In examples such as described with reference to FIGS. 1A-1E and 2A-2C, an unsaturated cyclic dione is coupled to a substrate via a linker, and a functionalized indole, functionalized indazole, or functionalized diene is reacted therewith to form a reaction adduct via which a functional group is coupled to the substrate. In other examples, such as described with reference to FIGS. 3A-3B, an indole or indazole is coupled to the substrate via a linker, and a functionalized unsaturated cyclic dione is reacted therewith to form a reaction adduct via which a functional group is coupled to the substrate. In other examples, such as described with reference to FIGS. 4A-4B, a diene is coupled to the substrate via a linker, and a functionalized unsaturated cyclic dione is reacted therewith to form a reaction adduct via which a functional group is coupled to the substrate.

FIGS. 1A-1E schematically illustrate example compositions and operations in a process for coupling functional groups to a substrate. Although FIGS. 1A-1E illustrate specific examples of molecules that may be used in the present compositions and operations, it will be appreciated that other molecules suitably may be used.

Referring now to FIG. 1A, composition 100 includes a plurality of unsaturated cyclic diones 110 coupled to substrate 101 via respective linkers (L). Illustratively, the unsaturated cyclic diones may have the structure:

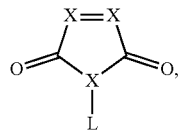

where L includes the linker to the substrate 101 and each X independently is CH or N. In some examples, such as illustrated in FIG. 1A, the unsaturated cyclic diones 110 may include TAD molecules having the structure:

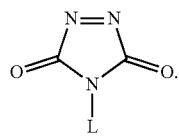

In other examples, unsaturated cyclic diones 110 may include maleimide molecules having the structure:

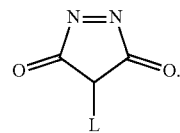

In still other examples, unsaturated cyclic diones 110 may include 4-cyclopentene-1,3-dione molecules having the structure:

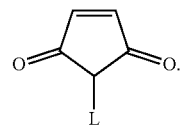

Nonlimiting examples of linkers (L) are provided elsewhere herein. Substrate 101 may include a polymer disposed on a solid support, or may include a solid support that does not have a polymer disposed thereon. In some examples, the solid support may include any substrate material such as described elsewhere herein. The polymer, if included, may include any suitable polymer such as described elsewhere herein, illustratively a polymer functionalized to include POSS. The substrate may be treated with a silane to facilitate capture of the polymer and/or the unsaturated cyclic dione. L may be coupled to substrate 101 (e.g., to a solid support or to a polymer disposed on a solid support) in any suitable manner. For example, a polymer brush may be grown using monomers with relevant functional groups.

The unsaturated cyclic diones may be reacted with indole or indazole molecules including a first functional group (F1) to form a first adduct coupling the first functional group to the substrate. For example, in a manner such as illustrated in FIG. 1A, TAD molecules 110 may be reacted with indole molecules 120 including a first functional group (F1) to form a first adduct coupling the first functional group to the substrate. The unsaturated cyclic diones may be contacted with indole or indazole molecules 120 that are dissolved in any suitable solvent (e.g., a polar protic solvent such as water or alcohol, or a polar aprotic solvent such as acetonitrile, ester, or ether) that is compatible with the dione molecules and the indole or indazole molecules, at any suitable reaction temperature, e.g., at room temperature. In the nonlimiting example illustrated in FIG. 1A, the indole molecules 120 may have the structure:

which may be referred to as 1H-indole, and where F1 includes the first functional group. However, the unsaturated cyclic diones may be reacted with any suitable indole or indazole, e.g., a molecule having the structure:

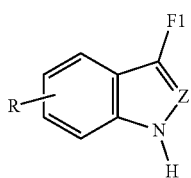

where R is H, an electron withdrawing group, or an electron donating group, and Z is CH or N. Illustratively, the indazole may have the structure:

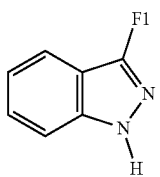

which may be referred to as 1H-indazole.

The first functional group may be or include any suitable molecule or molecules such as described elsewhere herein. In nonlimiting examples, the first functional group (F1) may be selected from the group consisting of: an oligonucleotide, a hydrophilic molecule (such as PEG), a hydrophilic macromolecule, a catalyst, and a label. Illustratively, the first functional group (F1) may be or include an oligonucleotide.

Reaction of the unsaturated cyclic diones with the indole or indazole may provide a composition including a plurality of first adduct molecules 130 which may have the structure:

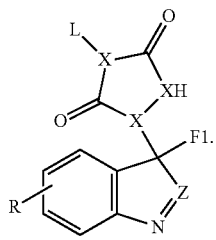

which may be referred to as a Michael-addition adduct, and where X, Z, R, L, and F1 are as defined elsewhere herein. Illustratively, in the specific example shown in FIG. 1B, reaction of TAD molecules 110 and indole molecules 120 may provide composition 100' including a plurality of first adduct molecules 130 which may have the structure:

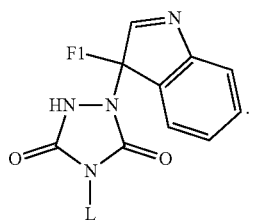

Other adducts coupling F1 to the substrate, e.g., using Michael addition reactions between unsaturated cyclic diones and indoles or indazoles, readily may be envisioned based on the teachings provided herein.

The reactions between the unsaturated cyclic dione molecules 110 and indole or indazole molecules 120 may be reversible, and may be referred to as "reversible Click" reactions. As such, in some examples, adduct molecules 130 may be heated to a suitable temperature to regenerate the unsaturated cyclic dione molecules 110 coupled to the substrate and cause dissociation of the indole or indazole molecules 120 (and the first functional group F1 coupled thereto) in a manner such as illustrated for TAD molecules remaining coupled substrate 101 and indole molecules dissociating in FIG. 1C. For example, substrate 101 may be heated to a temperature of at least 50° C., or a temperature of about 50° C. to about 100° C., or a temperature of about 60° C. to about 90° C., or a temperature of about 60° C. to about 80° C. to regenerate the unsaturated cyclic dione molecules 110 coupled to the substrate and cause dissociation of the indole or indazole molecules 120. As one option, after regenerating the unsaturated cyclic dione molecules 110, the dione molecules may be reacted with another functionalized indole or indazole in a manner such as described with reference to FIGS. 1A-1C. Such reaction similarly may be reversible, and as such the unsaturated cyclic dione molecules 110 again may be regenerated for use in further reactions.

Note that adduct molecules 130 may be significantly less reactive than the unsaturated cyclic diones 110, e.g., may be significantly less reactive than TAD. As such, the indole or indazole molecules 120 may be considered to "protect" the unsaturated cyclic diones (e.g., TAD molecules). Thus, in some examples, the unsaturated cyclic diones 110 may be considered to be "deprotected" by heating to reverse the "reversible Click" reactions, or by reacting adduct molecules 130 with dienes in a "transClick" reaction such as described further below. In this regard, note that indole or indazole molecules 120 that are used as protectants may include a functional group, or may not include a functional group. Additionally, in some examples only a subset of the indole or indazole molecules are dissociated from adduct molecules 130 (whether by "transClick" or "reversible Click") and the remaining indole molecules coupled to the substrate may continue to protect the unsaturated cyclic diones from participating in undesired chemical or biochemical reactions. In some examples, the indole or indazole molecules 120 include functional groups such as a hydrophilic molecule (such as PEG) which may inhibit fouling of the substrate and, in examples in which the substrate is to be used for polynucleotide sequencing, may help to improve sequencing quality for longer sequencing runs.

Figure 1D:
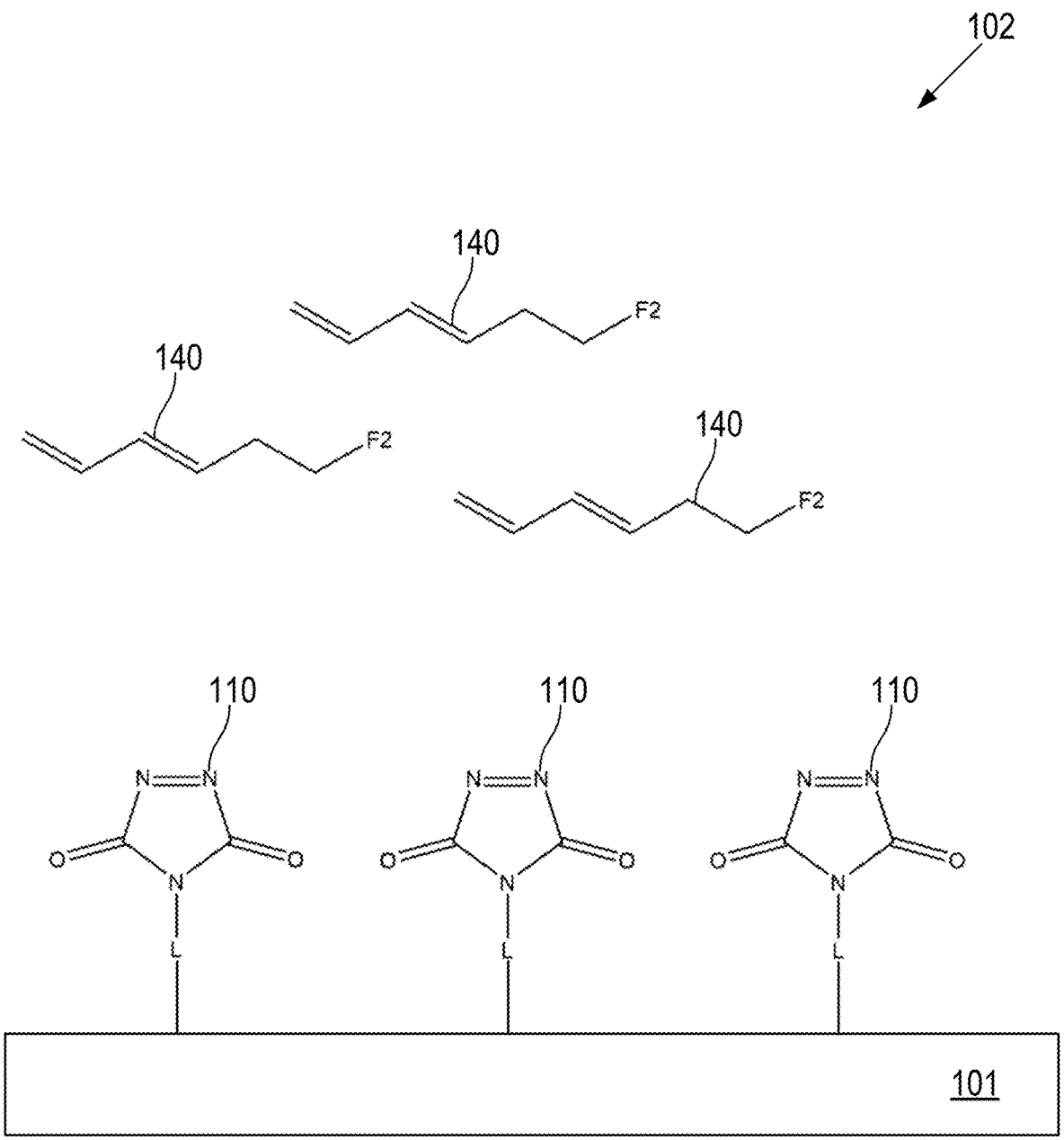

The unsaturated cyclic diones may be reacted with dienes including a second functional group (F2) to form a second adduct coupling the second functional group to the substrate. The dienes may include 1,3-dienes which may include substitutions on any of the carbons of the diene, and may include any suitable heteroatom substitution schemes that could be envisioned to increase the reactivity. In some examples, in a manner such as illustrated in FIG. 1D, TAD molecules 110 may be reacted with 1,3-dienes 140 including a second functional group (F2) to form a second adduct coupling the second functional group to the substrate. TAD molecules 110 may have been, but need not necessarily have been, previously reacted with indoles 120 to form adduct 130 prior to the TAD molecules 110 being regenerated in a manner such as described with reference to FIGS. 1A-1C. In composition 102 illustrated in FIG. 1D, TAD molecules 110 may be contacted with 1,3-diene molecules 140 that are dissolved in any suitable solvent (e.g., a polar protic solvent such as water or alcohol, or a polar aprotic solvent such as acetonitrile, ester, or ether) that is compatible with the TAD molecules and the diene molecules.

In the nonlimiting example illustrated in FIG. 1D, the 1,3-diene molecules 140 may have the structure:

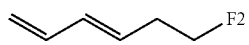

(trans,trans-1,3-hexadiene). However, it will be appreciated that many other dienes suitably may be used. For example, the diene molecules 140 instead may be 2,4-dienes, e.g., having the structure:

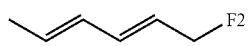

(trans-trans-2,4-hexadiene). In still other examples, the diene may include Danishefsky's diene, e.g., having the structure:

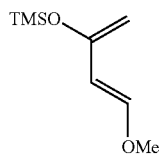

(1-methoxy-3-trimethylsiloxy-buta-1,3-diene). In yet other examples, the diene may include derivative of a Danishefky's diene, such as a Brassard diene, e.g., having the structure:

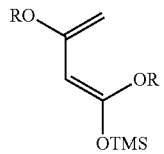

(1,3-alkoxy-1-trimethylsiloxy-1,3-butadiene) where at least one of the R groups may include F2 and another of the R groups may include, illustratively, a methyl or ethyl; or such as a Rawal diene, e.g., having the structure:

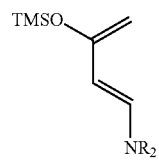

(1-dialkylamino-3-trimethylsiloxy-1,3-butadiene) where at least one of the R groups may include F2 and another of the R groups may include, illustratively, methyl or ethyl. Chan dienes may be used similarly.

In some examples, the second functional group (F2) of the diene may be selected from the group consisting of: an oligonucleotide, a hydrophilic molecule, a hydrophilic macromolecule, a catalyst, and a label. Illustratively, the second functional group is an oligonucleotide. In some examples in which the unsaturated cyclic diones 110 were regenerated from adducts 130 prior to reaction with diene molecules 140, the second functional groups (F2) of the diene molecules 140 may be different than the first functional groups (F1) of the indole molecules 120. Illustratively, the first functional group may include an oligonucleotide and the second functional group may include an element other than an oligonucleotide, such as a hydrophilic molecule, hydrophilic macromolecule, catalyst, or label. Or, the first functional group may include a first oligonucleotide and the second functional group may include a second oligonucleotide that is different than the first oligonucleotide. Alternatively, the first functional groups (F2) of the diene molecules 140 may be the same as the first functional groups (F1) of the indole molecules 120.

Figure 1E:
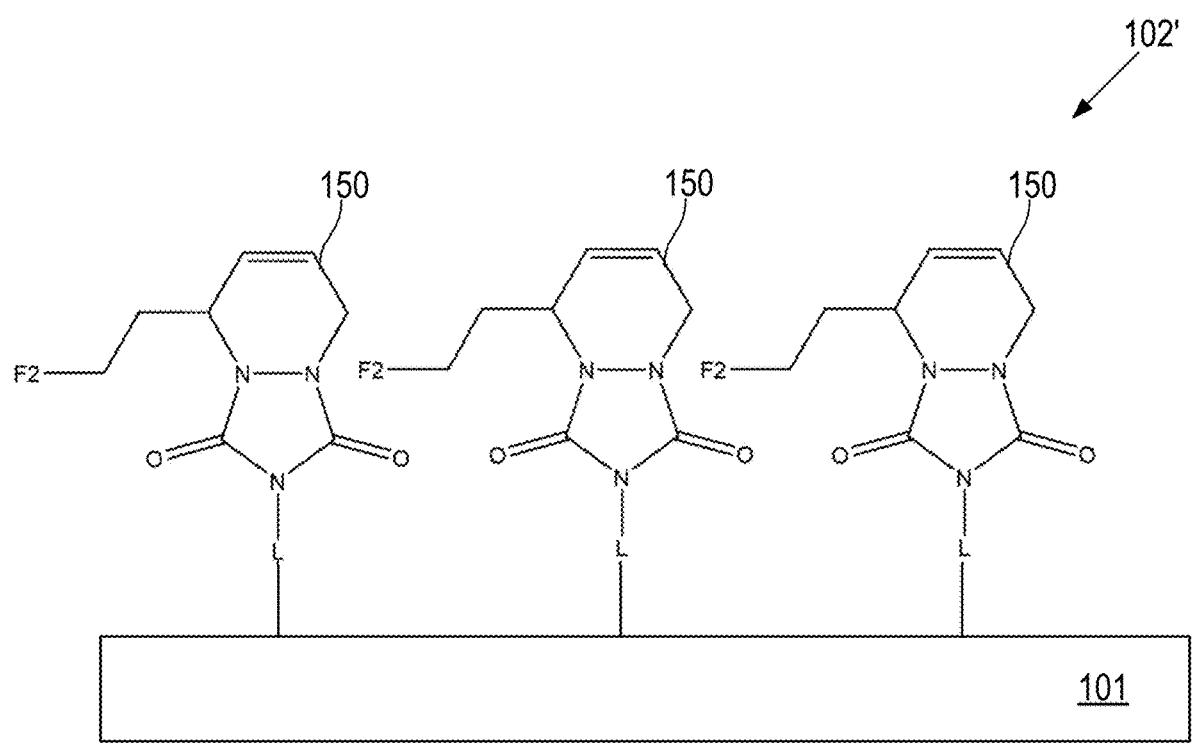

In the nonlimiting example illustrated in FIG. 1E, a [4+2] cyclization reaction of the TAD molecules 110 may provide composition 102' including a plurality of second adduct molecules 150 which may have the structure:

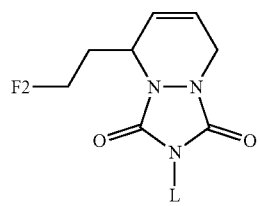

where L is a linker to the substrate and F2 is the second functional group. However, other adducts of reactions between other unsaturated cyclic diones and/or other dienes may be envisioned based on the present teachings. Illustratively, reaction of the unsaturated cyclic dione

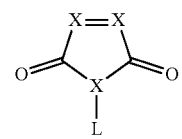

with trans,trans-1,3-hexadiene may generate the adduct:

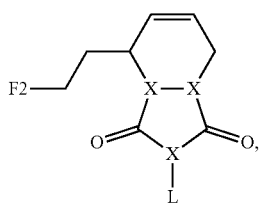

where X is CH or N. In examples in which the unsaturated cyclic dione is maleimide, the adduct may have the structure:

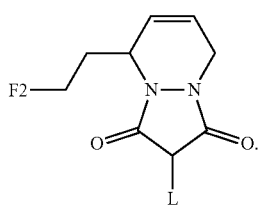

In examples in which the unsaturated cyclic dione is 4-cyclopentene-1,3-dione, the adduct may have the structure:

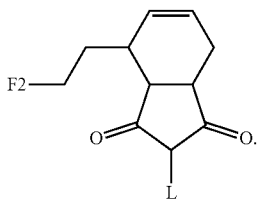

Figure 1F:
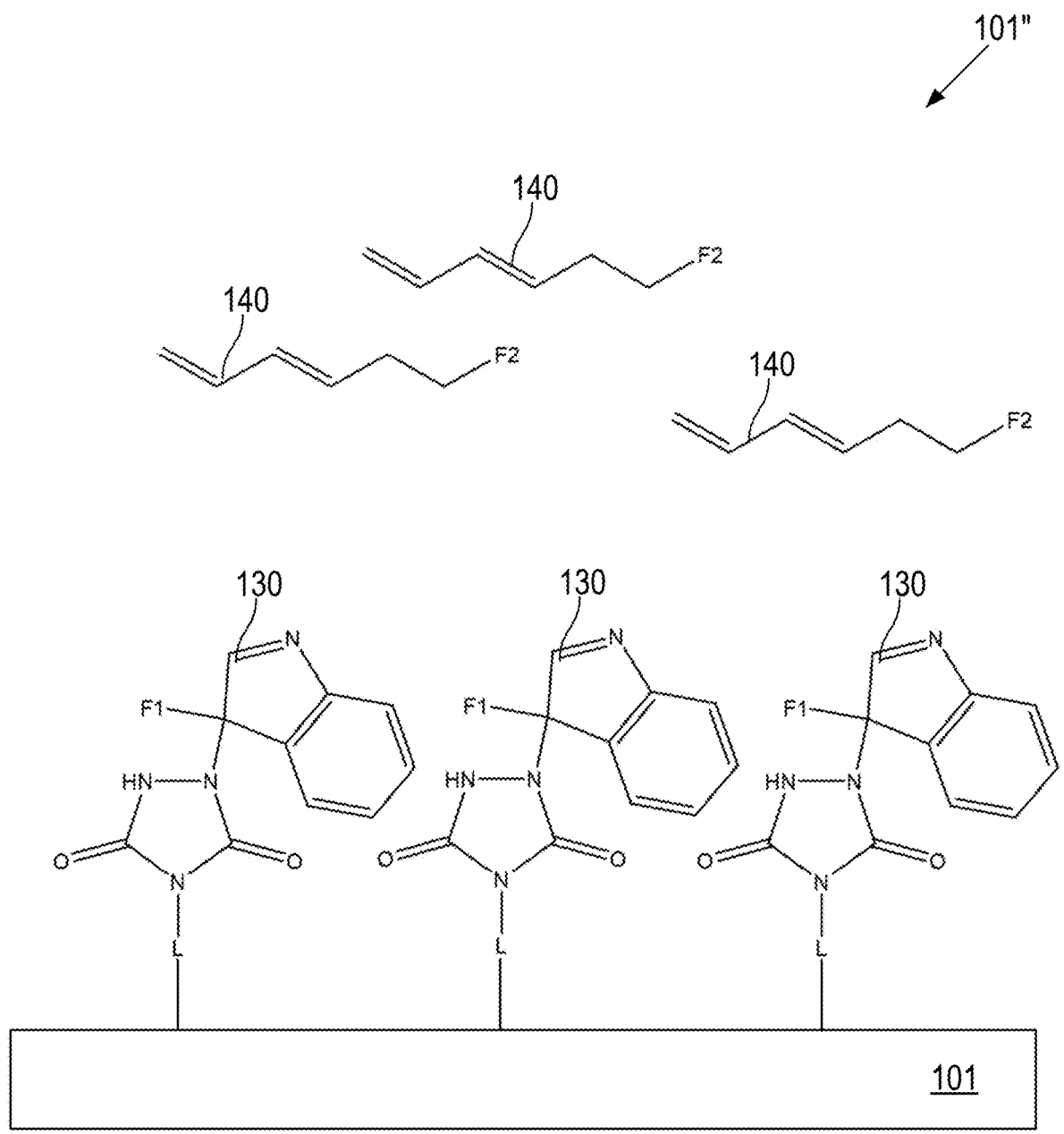

The reactions between the unsaturated cyclic diones 110 (e.g., TAD) and diene molecules 140 (e.g., 1,3-dienes) to form second adduct molecules 150, a nonlimiting example of which is illustrated in FIG. 1E, may be substantially irreversible. When such reactions are performed through the scheme illustrated in FIG. 1D (e.g., by contacting unsaturated cyclic diones 110 with diene molecules 140), such reactions may be referred to as "ultrafast Click" reactions. However, second adduct molecules 150 illustrated in FIG. 1E alternatively may be obtained through a different reaction scheme. More specifically, diene molecules 140 instead may be reacted with first adduct molecules 130, e.g., by contacting composition 100' with a suitable solvent including diene molecules 140 in a manner such as illustrated in FIG. 1F. In composition 101" illustrated in FIG. 1F, the diene molecules 140 may displace the indole or indazole molecules 120 from adduct molecules 130, causing the first functional group F1 to dissociate from substrate 101 and coupling the second functional group F2 to the substrate to form second adduct molecules 150 of composition 102' illustrated in FIG. 1E. As such, the indole molecules 120 may be considered to "protect" the unsaturated cyclic diones 110 (such as TAD) prior to reacting adduct molecules 130 with diene molecules 140.

Figure 2A:
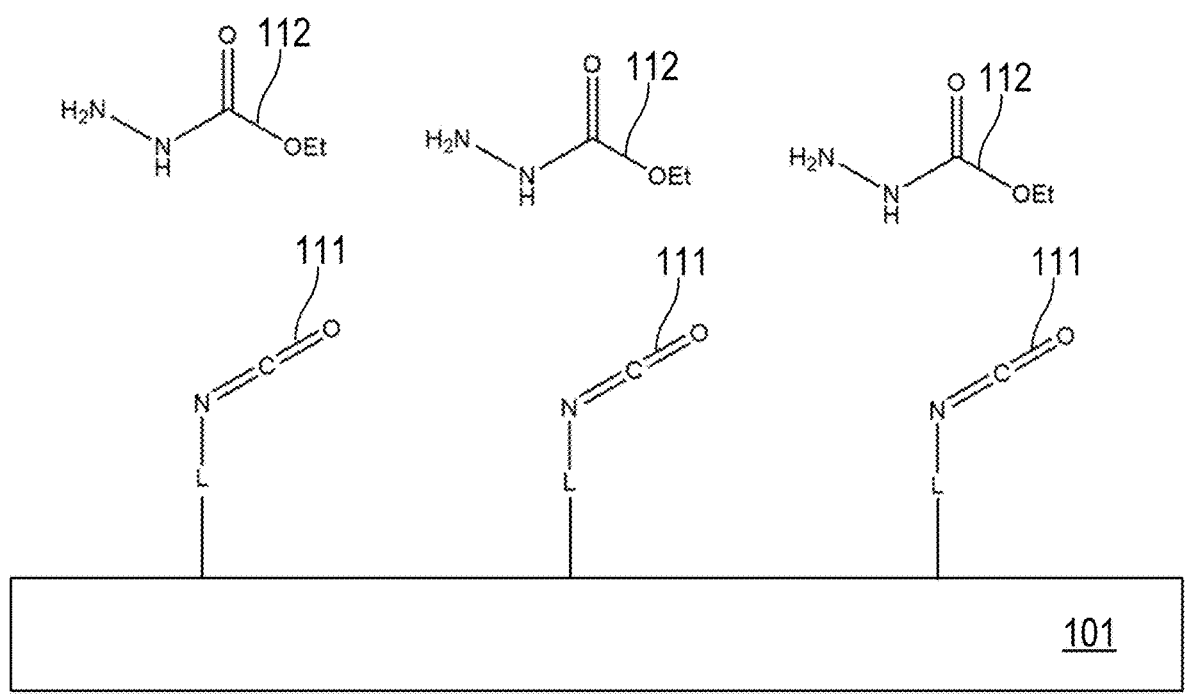
FIGS. 2A-2C schematically illustrate example compositions and operations in another process for coupling functional groups to a substrate.
Figure 2B:
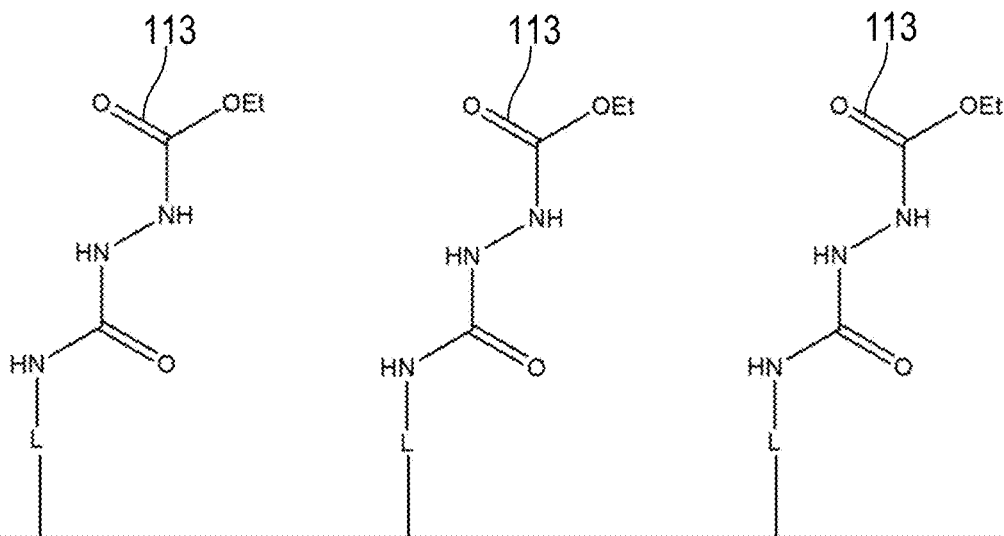
Figure 2C:
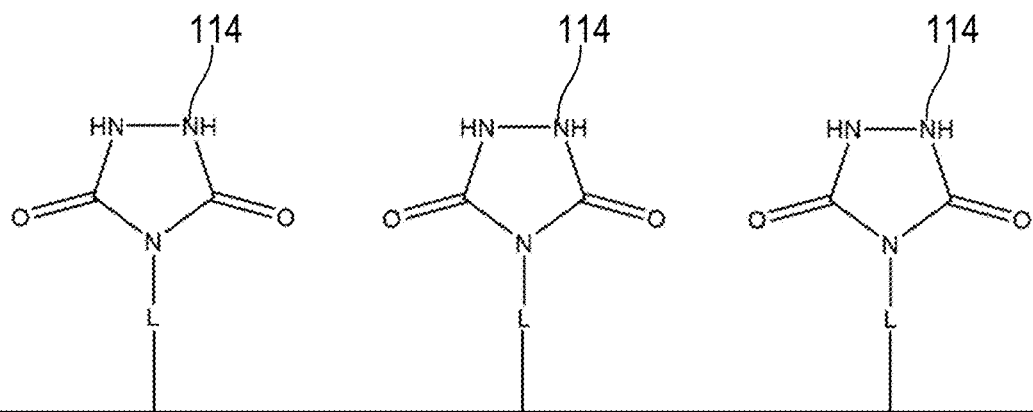

It will be appreciated that the unsaturated cyclic diones 110 coupled to substrate 101, such as described with reference to FIGS. 1A-1F, may be prepared using any suitable combination of operations. For example, TAD molecules 110 may be prepared via 4-substituted urazoles (where the 4-substituent of the urazole is coupled to the substrate, e.g., via linker L) via an oxidative mechanism. For example, FIGS. 2A-2C schematically illustrate example compositions and operations in another process for coupling functional groups to a substrate. As illustrated in FIG. 2A, substrate 101 may be functionalized so as to include isocyanate 111 coupled thereto via linker L, e.g., using a commercially available isocyanate from SiSiB® Silicones—PCC Group (Nanjing, China). Isocyanate 111 may be contacted with, and undergo a condensation reaction with, compound 112 having structure:

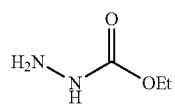

which may be referred to as N-amino ethoxy carbamate or hydrazine carbamate. In some examples, compound 112 may be obtained by reacting hydrazine ($N_2H_4$) with the following compound:

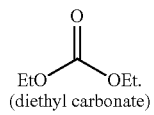
(diethyl carbonate)

As illustrated in FIG. 2B, the reaction product 113 of isocyanate 111 and compound 112 may have the structure:

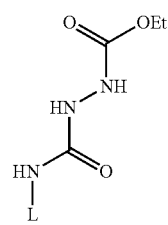

where L is the linker to the substrate. Reaction product 113 then may be subjected to a base-mediated cyclization reaction to form a 4-substituted urazole 114, coupled to the substrate in a manner such as illustrated in FIG. 2C, and having the structure:

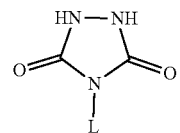

where L is the linker to the substrate. The 4-substituted urazoles 114 may be oxidized to form TAD molecules 110 coupled to substrate 101 via linkers L, such as described with reference to FIGS. 1A and 1D. A wide variety of oxidative conditions may be used to convert 4-substituted urazoles 114 to TAD molecules 110, such as using in-situ generated $N_2O_4$ oxidation, peracid conditions, hypervalent iodide species, oxones, hypochlorites, 1,4-diazabicyclo[2.2.2]octane bromine (DABCO-Br), or chlorates.

Note that 4-substituted urazoles 114 may be significantly less reactive than TAD molecules 110. As such, the 4-substituted urazoles 114 may be considered to provide a "protective" group, and may not be oxidized to form TAD molecules 110 until immediately before it is intended to react the TAD molecules with dienes or indoles in a manner such as described with reference to FIGS. 1A-1F. Schemes for coupling other types of unsaturated cyclic diones, such as those described elsewhere herein, suitably may be used.

As noted further above, although in some examples the unsaturated cyclic dione is coupled to the substrate and reacted with a functionalized diene, indazole, or indole that is in solution, in other examples the diene, indazole, or indole may be coupled to the substrate and reacted with a functionalized unsaturated cyclic dione that is in solution.

Figure 3A:
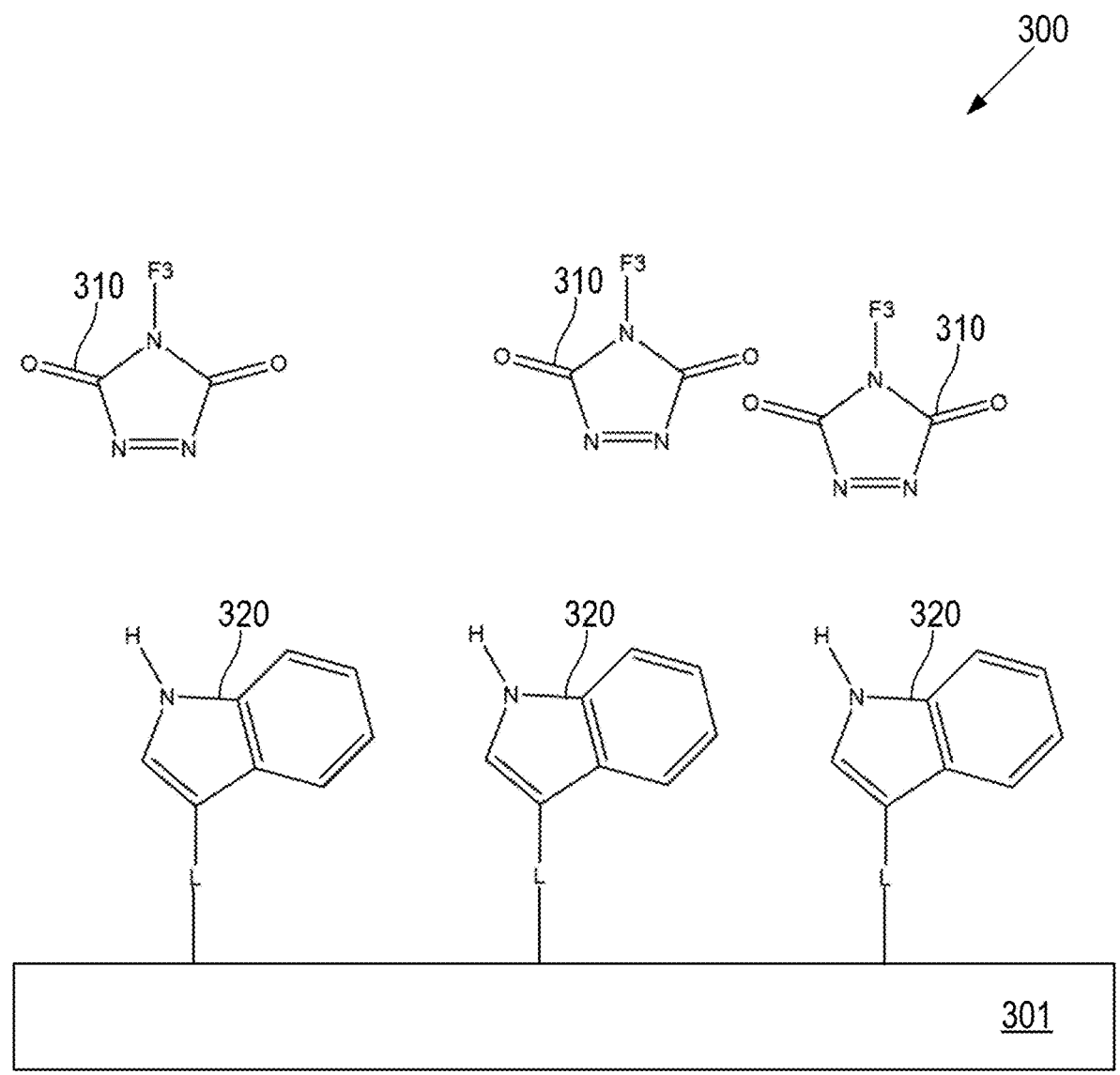
FIGS. 3A-3B schematically illustrate example compositions and operations in another process for coupling functional groups to a substrate.
Figure 3B:
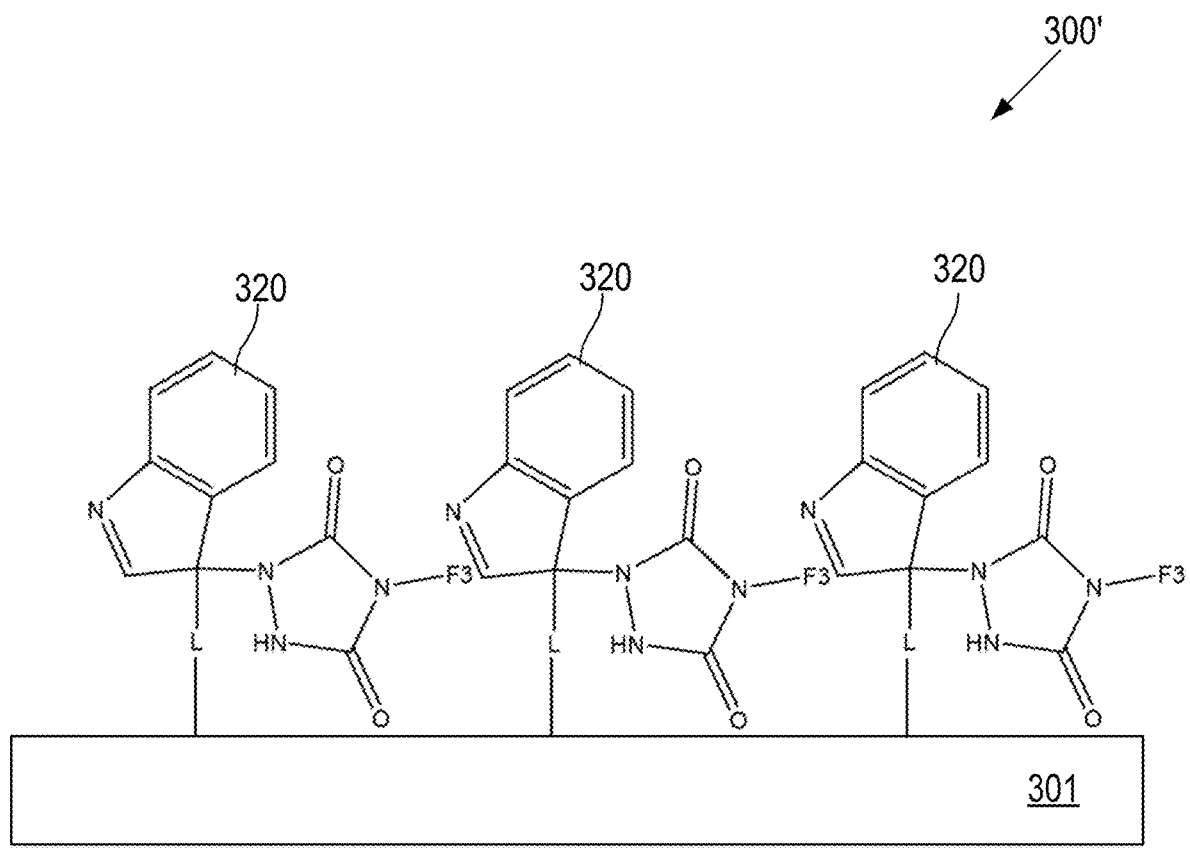

For example, FIGS. 3A-3B schematically illustrate example compositions and operations in another process for coupling functional groups to a substrate. Referring now to FIG. 3A, composition 300 includes a plurality of indole or indazole molecules 320 coupled to substrate 301 via respective linkers (L). The indole or indazole molecules 320 may have the structure:

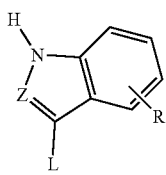

where Z is CH or N; L includes a linker to the substrate; and R is H, an electron withdrawing group, or an electron donating group. In the nonlimiting example illustrated in FIG. 3A, the indole molecules 320 may have the structure:

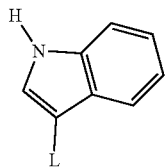

where L is a linker to substrate 301. Other example structures for indoles and indazoles are provided with reference to FIGS. 1A-1F. Nonlimiting examples of L and substrate are provided elsewhere herein. Substrate 301 may include a polymer (e.g., a polymer functionalized to include POSS) disposed on a solid support, or may include a solid support that does not have a polymer disposed thereon.

The indole or indazole molecules may be reacted with the unsaturated cyclic dione including a functional group (F3) to form an adduct coupling the functional group to the substrate. For example, in a manner such as illustrated in FIG. 3A, indole molecules 320 are reacted with TAD molecules 310 including a functional group (F3) to form an adduct coupling the functional group to the substrate. For example, the indole or indazole molecules 320 may be contacted with unsaturated cyclic diones 310 that are dissolved in any suitable solvent (e.g., a polar protic solvent such as water or alcohol, or a polar aprotic solvent such as acetonitrile, ester, or ether) that is compatible with the unsaturated cyclic dione molecules and the indole or indazole molecules.

The unsaturated cyclic dione may have the structure:

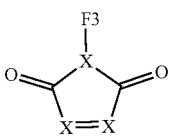

where X is CH or N, and where F3 includes the functional group. In the nonlimiting example illustrated in FIG. 3A, the unsaturated cyclic dione may include TAD molecules 310 having the structure:

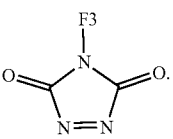

Alternatively, the unsaturated cyclic dione may include a maleimide or 4-cyclopentene-1,3-dione that is functionalized to include F3 at the 4 position. The functional group may be or include any suitable molecule or molecules such as described elsewhere herein. In nonlimiting examples, the functional group (F3) may be selected from the group consisting of: an oligonucleotide, a hydrophilic molecule, a hydrophilic macromolecule, a catalyst, and a label. Illustratively, functional group (F3) may be or include an oligonucleotide.

Reaction of the unsaturated cyclic dione in solution, and the indole or indazole molecules coupled to the substrate, may provide a composition including a plurality of adduct molecules which may have the structure:

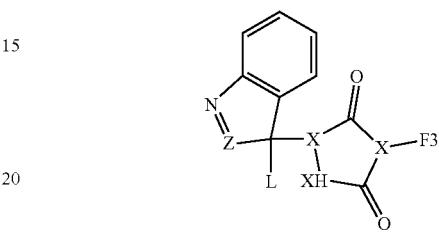

where Z is CH or N; L includes a linker to the substrate; R is H, an electron withdrawing group, or an electron donating group; F3 includes a functional group, and each X independently is CH or N. In the nonlimiting example illustrated in FIG. 3B, reaction of the TAD molecules 310 and the indole molecules 320 may provide composition 300' including a plurality of adduct molecules 330 which may have the structure:

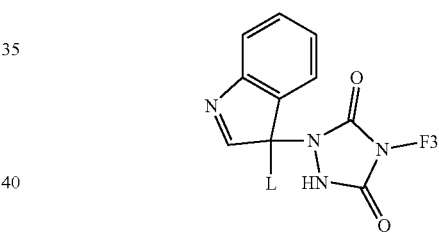

where L is the linker to the substrate and F3 is the functional group.

As noted elsewhere herein, the reactions between unsaturated cyclic diones and indole or indazole molecules may be reversible, and may be referred to as "reversible Click" reactions. As such, in some examples, the adducts of such reactions may be heated to a suitable temperature to regenerate the indole or indazole molecules coupled to the substrate and cause dissociation of the unsaturated cyclic diones (and the functional groups F3 respectively coupled thereto) in a manner similar to that described with reference to FIG. 1C. For example, substrate 301 may be heated to a temperature of at least 50° C., or a temperature of about 50° C. to about 100° C., or a temperature of about 60° C. to about 90° C., or a temperature of about 60° C. to about 80° C., or a temperature of about 80° C. to about 100° C., or a temperature of about 90° C. to about 100° C., to regenerate the indole or indazole molecules 320 coupled to the substrate and cause dissociation of the unsaturated cyclic dione (e.g., TAD) molecules 310. As one option, after regenerating the indole or indazole molecules 320, the indole or indazole molecules may be reacted with another functionalized unsaturated cyclic dione molecule in a manner such as described with reference to FIG. 3A. Such reaction similarly may be reversible, and as such the indole or indazole molecules 320 again may be regenerated for use in further reactions, e.g., for reaction with second unsaturated cyclic dione molecules to form second adducts. The second unsaturated cyclic dione molecules may include a functional group, e.g., a functional group selected from the group consisting of: a second oligonucleotide, a hydrophilic molecule, a hydrophilic macromolecule, a catalyst, and a label. The second oligonucleotide may have the same sequence, or a different sequence, than an oligonucleotide that was coupled to earlier-coupled unsaturated cyclic diones. In examples in which the unsaturated cyclic dione includes TAD, the TAD molecules may be prepared similarly as described with reference to FIGS. 2A-2C, e.g., may be prepared by providing a 4-substituted urazole, where the 4-substituent is the functional group (such as an oligonucleotide), and oxidizing the 4-substituted urazole to form the TAD including the functional group F3, e.g., oligonucleotide.

Figure 4A:
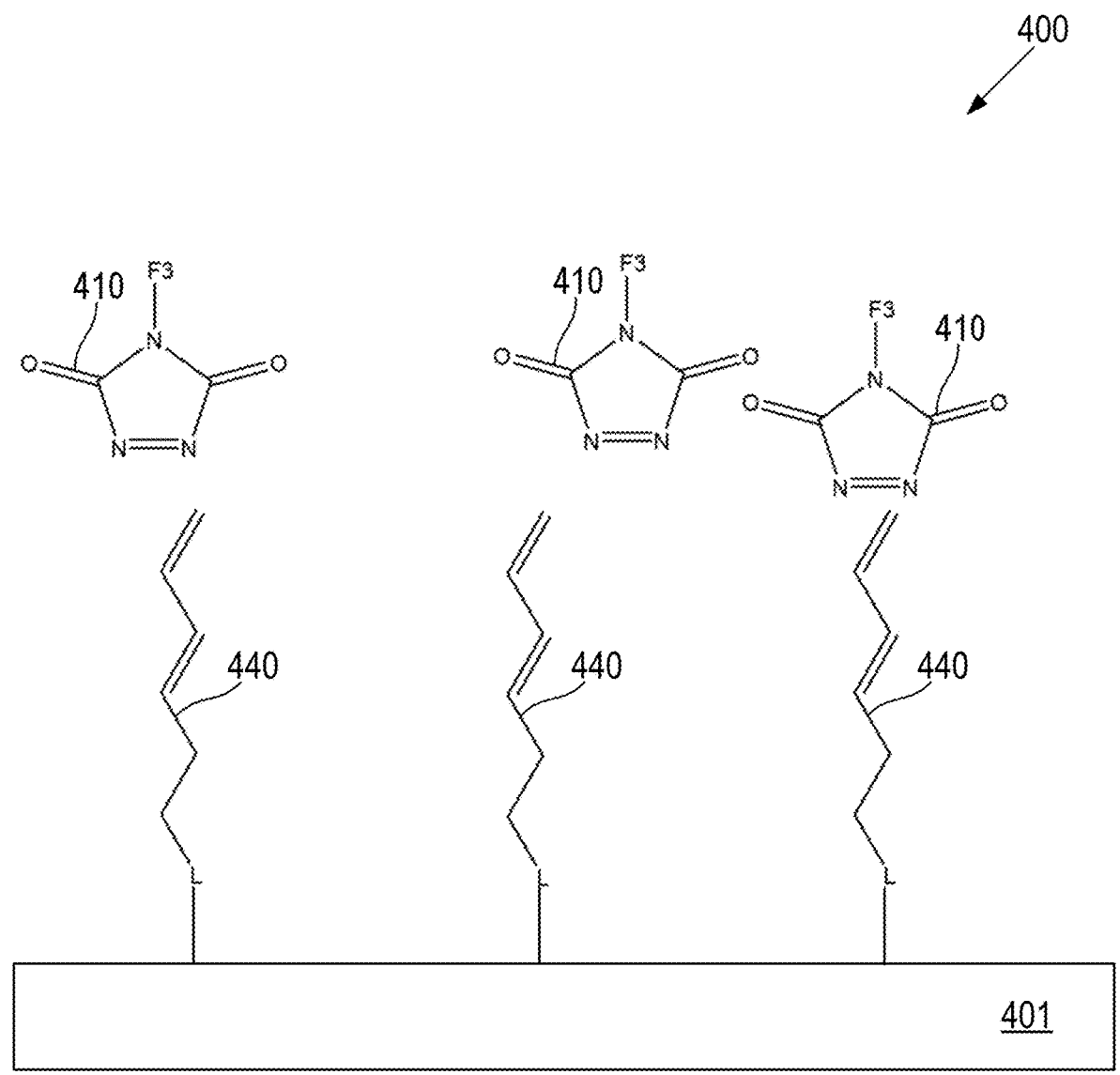
FIGS. 4A-4B schematically illustrate example compositions and operations in another process for coupling functional groups to a substrate.
Figure 4B:
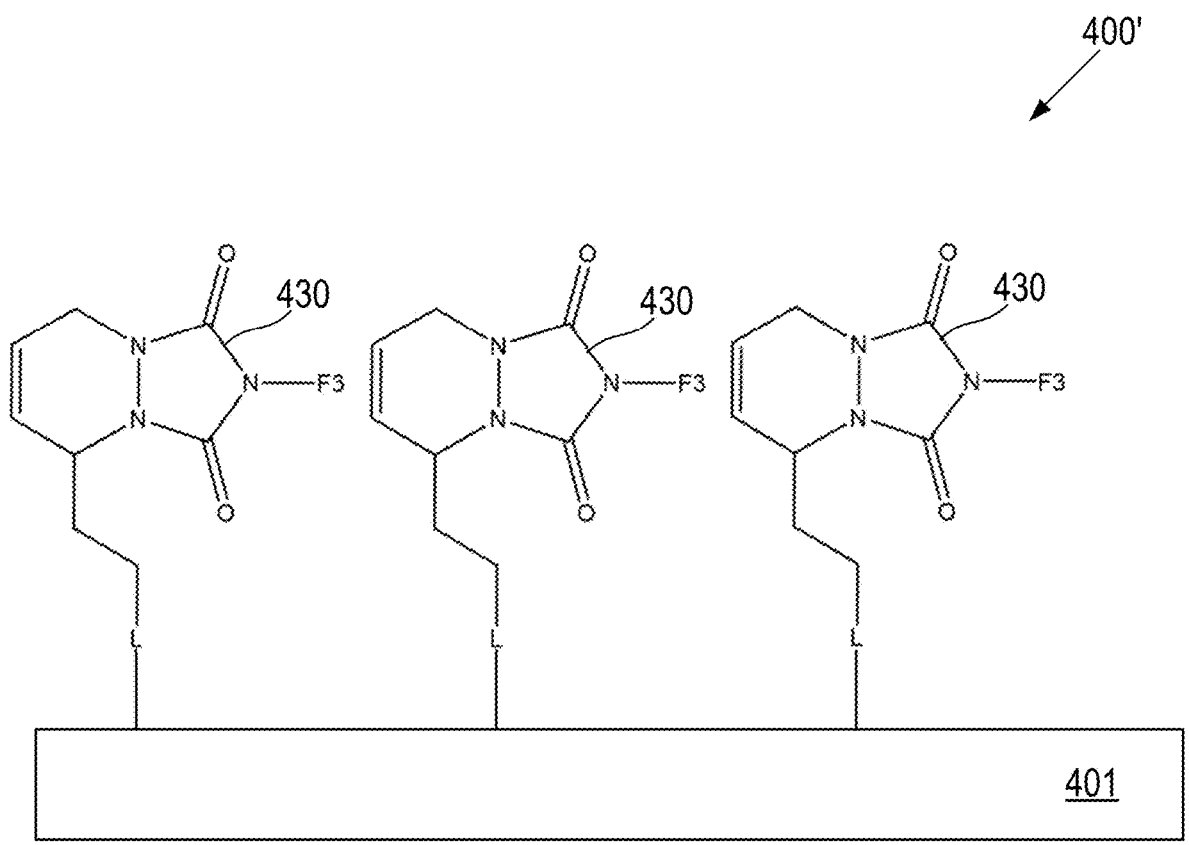

FIGS. 4A-4B schematically illustrate example compositions and operations in another process for coupling functional groups to a substrate. More specifically, a diene may be coupled to the substrate, and an unsaturated cyclic dione including a functional group may be reacted with the diene to couple the functional group to the surface. Examples of diene molecules provided with reference to FIGS. 1A-1F may be functionalized to include linker L coupling the dienes to the surface, instead of including a functional group themselves. Referring now to FIG. 4A, composition 400 includes a plurality of diene molecules 440 coupled to substrate 401 via respective linkers (L). In the illustrated example, the diene molecules 440 may have the structure:

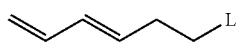

where L is a linker to substrate 401, although any other suitable 1,3-diene, 2,4-diene, Danishefsky's diene, Brassard diene, or Rawal diene may be used instead. Nonlimiting examples of L and substrate are provided elsewhere herein. Substrate 401 may include a polymer (e.g., a polymer that is functionalized to include POSS) disposed on a solid support, or may include a solid support that does not have a polymer disposed thereon.

In a manner such as illustrated in FIG. 4A, the diene molecules 440 are reacted with unsaturated cyclic dione (e.g., TAD) molecules 410 including a functional group (F3) to form an adduct coupling the functional group to the substrate. For example, the diene molecules 440 coupled to the substrate may be contacted with unsaturated cyclic dione molecules 410 that are dissolved in any suitable solvent (e.g., a polar protic solvent such as water or alcohol, or a polar aprotic solvent such as acetonitrile, ester, or ether) that is compatible with the unsaturated cyclic dione molecules and the diene molecules. The unsaturated cyclic dione molecules may have the structure:

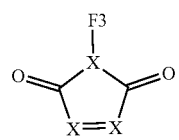

where X is CH or N, and F3 includes the functional group. In the nonlimiting example illustrated in FIG. 4A, the unsaturated cyclic diones may include TAD molecules 410 having the structure:

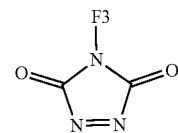

where F3 includes the functional group. In still other examples, the unsaturated cyclic diones may include maleimide:

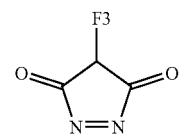

or 4-cyclopentene-1,3-dione:

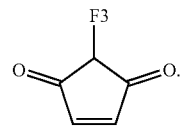

The functional group may be or include any suitable molecule or molecules such as described elsewhere herein. In nonlimiting examples, the functional group (F3) may be selected from the group consisting of: an oligonucleotide, a hydrophilic molecule, a hydrophilic macromolecule, a catalyst, and a label. Illustratively, functional group (F3) may be or include an oligonucleotide.

Reaction of the unsaturated cyclic diones and the diene molecules may provide a composition including a plurality of adduct molecules which may have the structure:

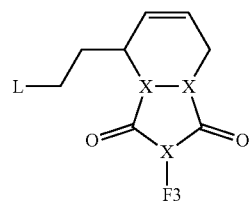

where each X independently is CH or N; L includes the linker to the substrate; and F3 includes the functional group. In the nonlimiting example illustrated in FIG. 4B, reaction of TAD molecules 410 and diene molecules 440 may provide composition 400' including a plurality of adduct molecules 430 which may have the structure:

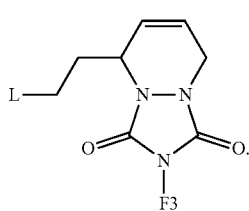

Other adducts between other dienes and other unsaturated cyclic diones readily may be envisioned based on the teachings herein. The reactions between the unsaturated cyclic diones and diene molecules may be substantially irreversible, and may be referred to as "ultrafast Click" reactions.

Methods of Using Compositions Including Functional Groups Coupled to Substrates

As noted elsewhere herein, an oligonucleotide is one nonlimiting example of a functional group that may be coupled to a substrate, e.g., in a manner such as described with reference to FIGS. 1A-1F, 2A-2C, 3A-3B, or 4A-4B. Oligonucleotides coupled to substrates in a manner such as described herein may be used in a variety of amplification techniques. Example techniques that can be used include, but are not limited to, polymerase chain reaction (PCR), rolling circle amplification (RCA), multiple displacement amplification (MDA), or random prime amplification (RPA), or a combination thereof. In some examples, one or more primers used for amplification may be coupled to the substrate. Formats that utilize two or more species of attached primer enable bridge amplification (BridgeAmp) or kinetic exclusion amplification (ExAmp), in which amplicons may form bridge-like structures between two attached primers that flank the template sequence that has been copied. Amplification can also be carried out with one amplification primer attached to a substrate and a second primer in solution (e.g., emulsion PCR).

Additionally, or alternatively, oligonucleotides coupled to substrates in a manner such as described herein may be used for determining the sequence of a target polynucleotide. For example, a target polynucleotide may be coupled (e.g., hybridized) to one of a plurality of primers covalently bound to a substrate in a manner such as described herein. The target polynucleotide may be amplified using the plurality of primers to form a cluster of substrate-bound amplicons. The cluster of substrate-bound amplicons may be contacted with labeled nucleotides (e.g., fluorescently labeled nucleotides) and a polymerase such that a detectable signal (e.g., fluorescence) is generated while a nucleotide is incorporated by the polymerase, and such signal may be used to identify the nucleotide and thereby determine a nucleotide sequence of the target polynucleotide.

WORKING EXAMPLES

Additional examples are disclosed in further detail in the following examples, which are not in any way intended to limit the scope of the claims.

Example 1. Block Copolymer Coupled to TAD Including Oligonucleotide

In one example, a first block copolymer (BCP1) is prepared that includes a diene, and the diene then is reacted with TAD that includes an oligonucleotide (P5 or P7 primer) to form a second block copolymer (BCP2) using the following reaction scheme:

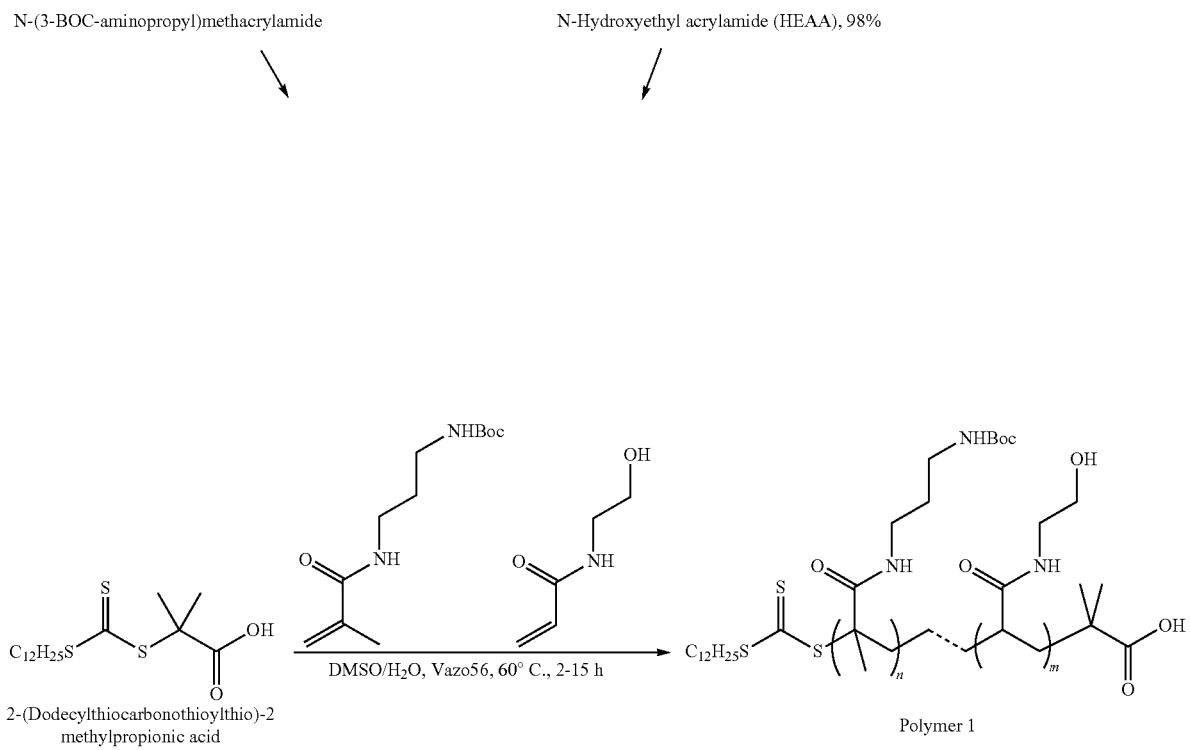

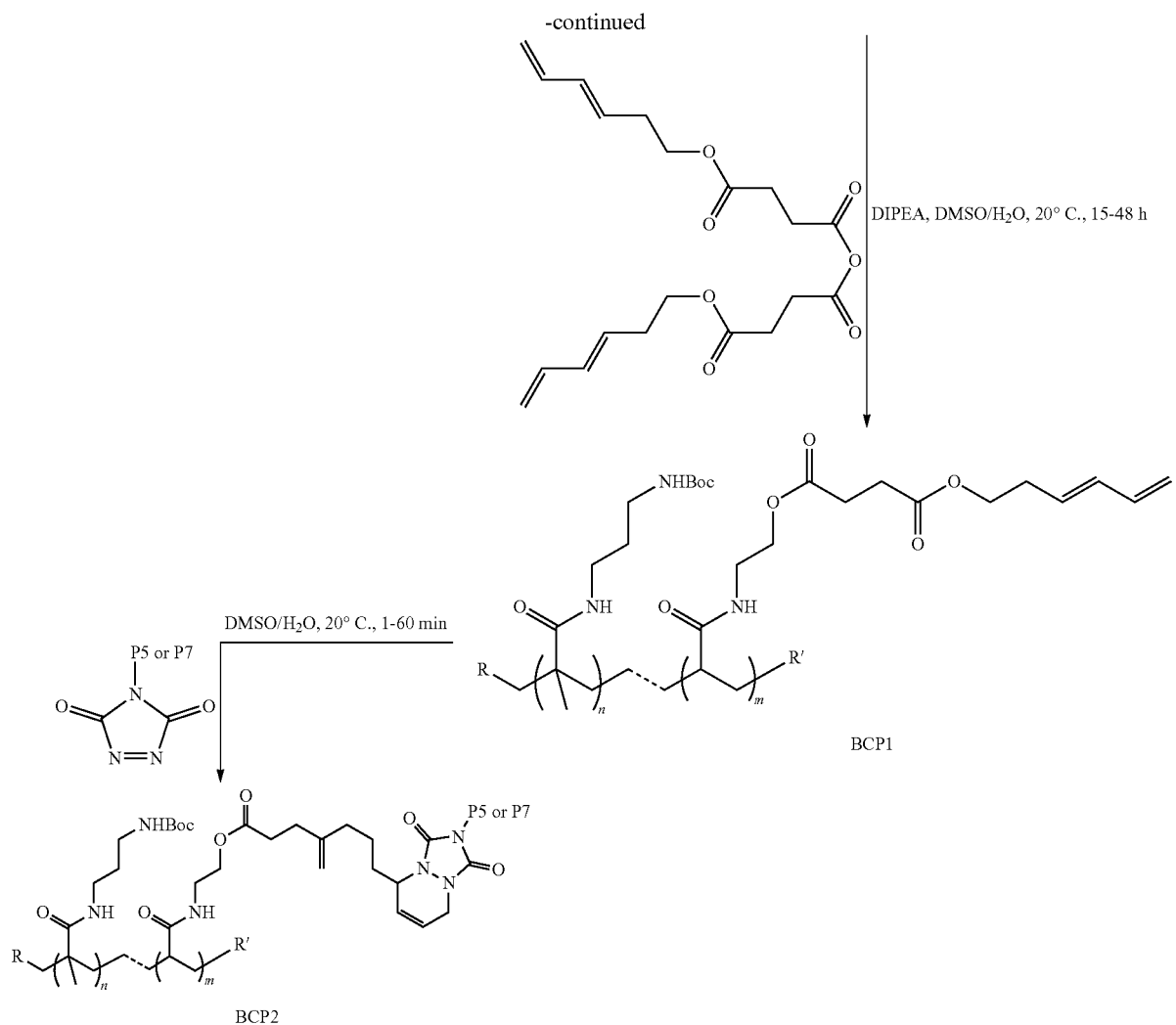

The NH₂ group of BCP2 is reacted with a substrate to covalently couple BCP2 to a glass or silica support. The reaction is performed on an attached isocyanate, activated carboxylic acid, or Michael acceptor. There is a clear visual indication of the TAD-diene reaction because the TAD molecules are deeply colored (red-purple) and upon their reaction (consumption) the solution gradually becomes colorless. The concentration of TAD molecules including oligonucleotides is monitored using UV or colorimetric monitoring and may be topped off in real time.

From this reaction scheme, it may be understood that an unsaturated cyclic dione such as TAD, including a desired functional group, such as an oligonucleotide (e.g., primer), may be reacted with a diene that is coupled to a substrate, such as a polymer disposed on a solid support, so as to couple the functional group to the substrate.

Example 2. Patterned Wells Coupled to TAD Including Oligonucleotide

Figure 5:
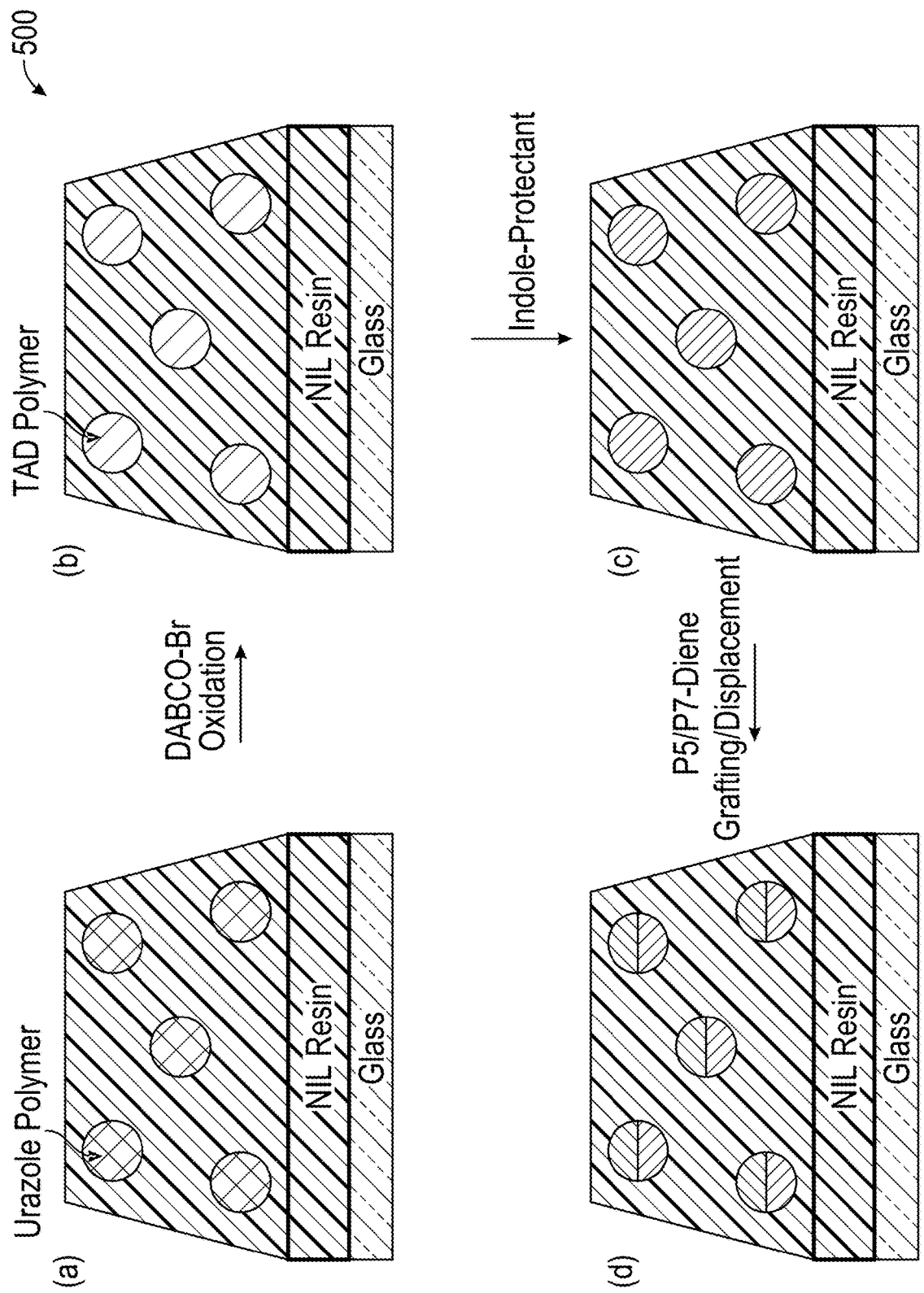
FIG. 5 schematically illustrates example compositions and operations in another process for coupling functional groups to a substrate.

FIG. 5 schematically illustrates example compositions and operations in another process for coupling functional groups to a substrate. Composition (a) illustrated in FIG. 5 includes a glass solid support having a polymer resin disposed thereon which was patterned using nano-imprint lithography (NIL) to form wells. Methods of patterning using NIL are described in WO2018/119053 and WO2018/118932, the entire contents of each of which are incorporated by reference herein. Methods of preparing a substrate are described in WO2014/133905, the entire contents of which are incorporated by reference herein. In the present example, the wells include a polymer coupled to 4-substituted urazole ("urazole polymer") such as described with reference to FIGS. 2A-2C. Composition (a) is oxidized using DABCO-Br to form composition (b) in which the wells include the polymer coupled to TAD molecules ("TAD polymer") such as described with reference to FIG. 1A. Composition (b) is reacted with indole molecules ("indole protectant") that do not have a functional group, to form composition (c) in which the wells include the polymer coupled to the adduct of the TAD-indole reaction such as described with reference to FIG. 1B, but omitting the functional group F1. Composition (c) is reacted with Example 3's diene functionalized to include oligonucleotide primers (P5/P7) ("P5/P7-diene Grafting/displacement"), in a manner such as described with reference to FIG. 1F to form composition (d) in which the wells include the polymer coupled to the TAD-diene adduct such as described with reference to FIG. 1E. In some examples, a portion of the nanowells would be functionalized in this method, leaving a remaining number of TAD moieties available for reaction.

The indole "reversible Click" reaction to form composition (c) is mild and may be conducted at room temperature. A large excess of the indole molecules may be used so as to provide complete, or substantially complete, protection of the polymer-coupled TAD molecules thereby preventing or inhibiting subsequent reaction of these molecules during downstream chemistry or biochemistry operations. Additionally, the "transClick" reaction of the indole-TAD adducts of composition (c) with functionalized dienes to form composition (d) may be a specific and substantially irreversible exchange reaction, which also is mild, non-etching and thus compatible with many different types of substrates, and may be conducted in minutes at room temperature. The oligonucleotide-functionalized dienes displace at least some of the indole protectant molecules that previously were coupled to the substrate.

From this reaction scheme, it may be understood that a diene including a desired functional group, such as an oligonucleotide (e.g., primer), may be reacted with an indole-protected TAD that is coupled to a substrate, such as a polymer disposed on a solid support, so as to couple the functional group to the substrate.

Example 3. Block Copolymer Coupled to Diene Including Oligonucleotide

In another example, a first block copolymer (BCP1) is prepared that includes a 4-substituted urazole, the urazole then is oxidized using DABCO-Br (made by reacting DABCO with $Br_2$ in a suitable solvent such as DCM or $CHCl_3$) to form a third block copolymer (BCP3) including TAD, and the TAD reacted with a diene including an oligonucleotide (P5 or P7 primer) to form a fourth block copolymer (BCP4) using the following reaction scheme:

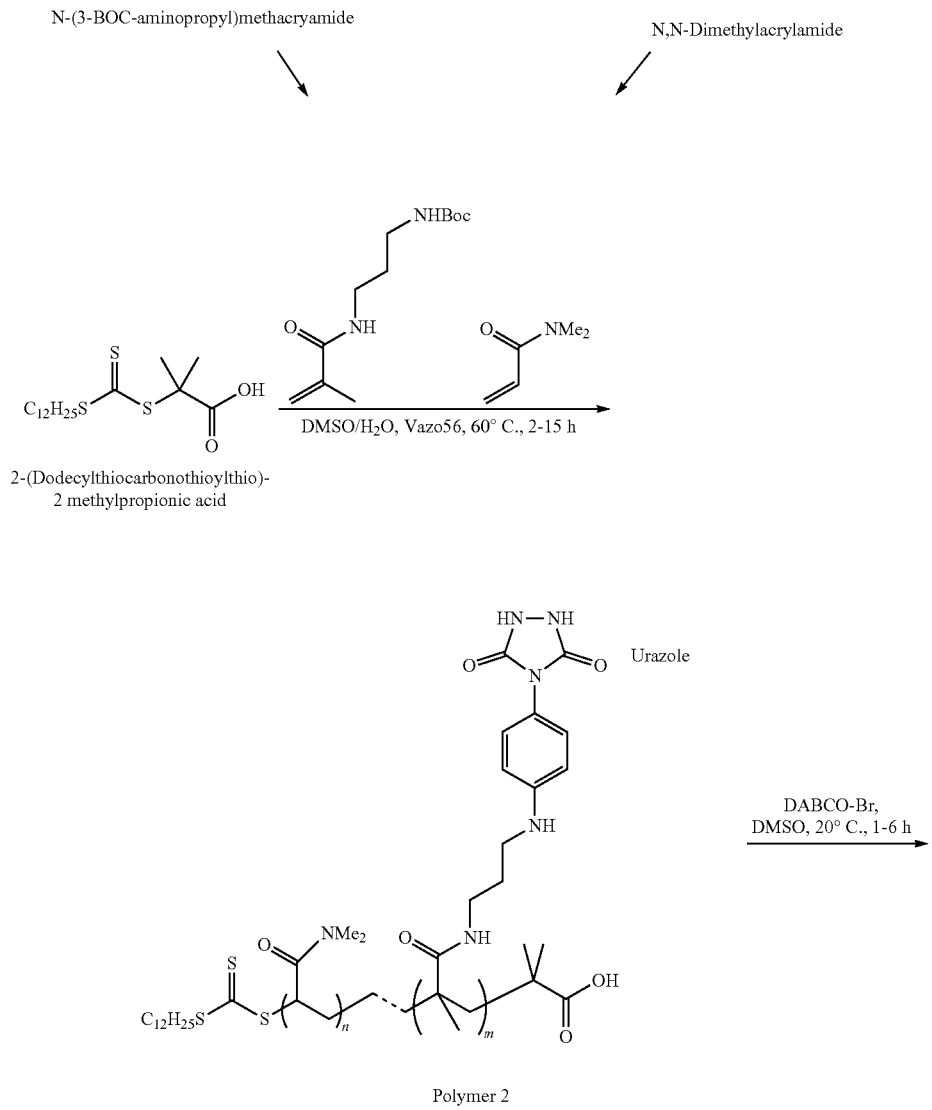

Polymer 2

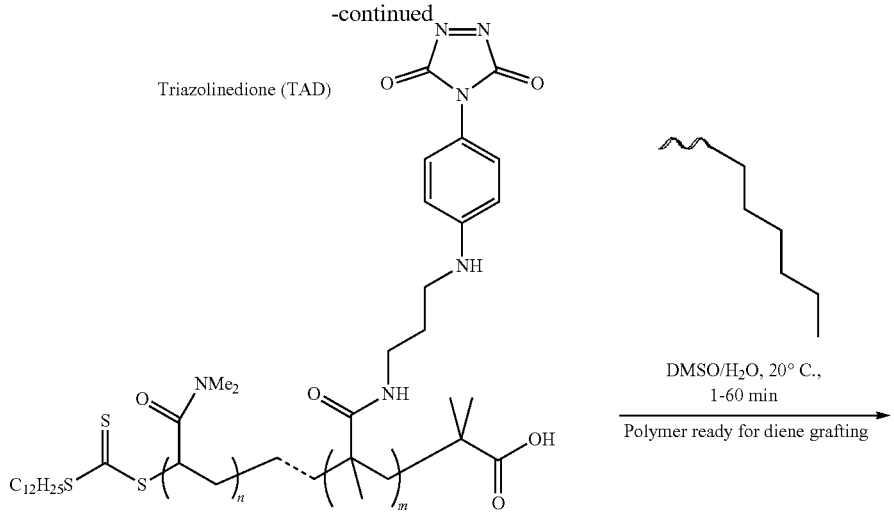

Triazolinedione (TAD)

BCP3

DMSO/H₂O, 20° C.,
1-60 min
Polymer ready for diene grafting

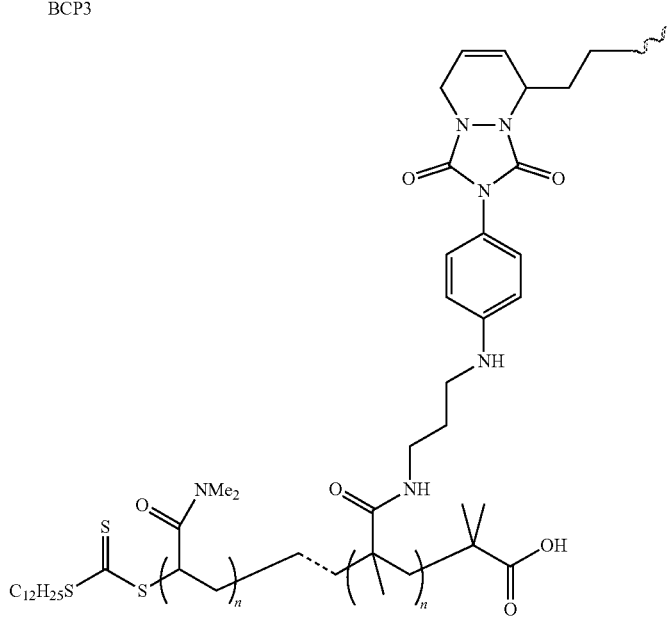

BCP4

The NH₂ group of BCP4 is reacted with a substrate to covalently couple BCP4 to a solid support in the manner described in Example 1. Additional reactions are performed in accordance with the schemes illustrated below to make TAD/unsaturated cyclic dione-containing polymers. The first scheme illustrated below uses reversible addition-fragmentation chain-transfer (RAFT) polymerization. These polymers are then reacted with dienes to form oligo-functionalized materials that are attached with surfaces, using similar chemistry (i.e. covalent attachment through remaining TAD units, not all of which are consumed during the polymer coating step, therefore leaving a majority remaining for reaction with the diene oligos. The subsequent scheme illustrated below details a method to make the monomer Az-TAD used in the first reaction scheme below.

N,N-Dimethylacrylamide

-continued
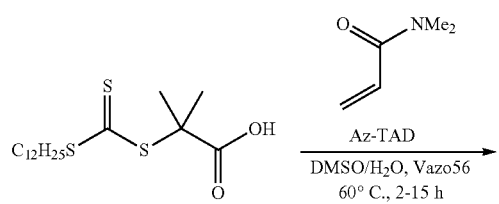
2-(Dodecylthiocarbonothioylthio)-
2-methylpropionic acid
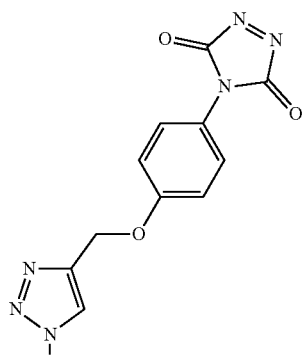
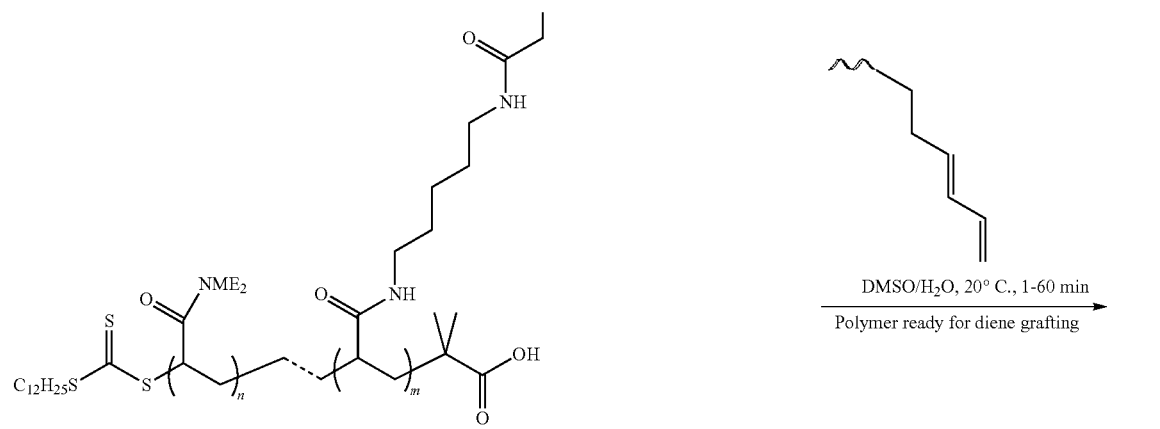
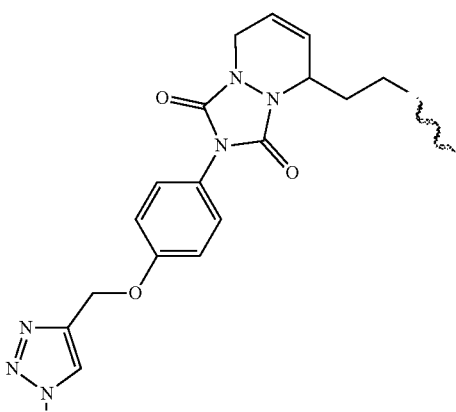

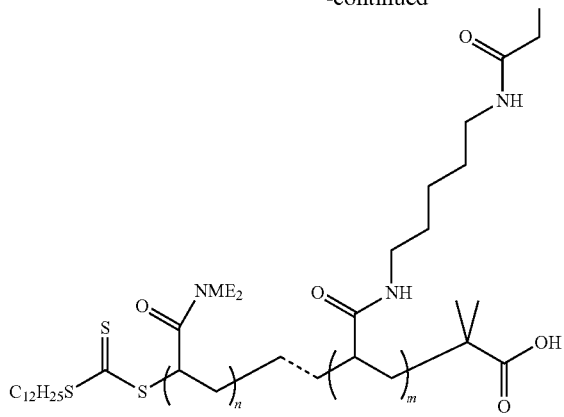
BCP4
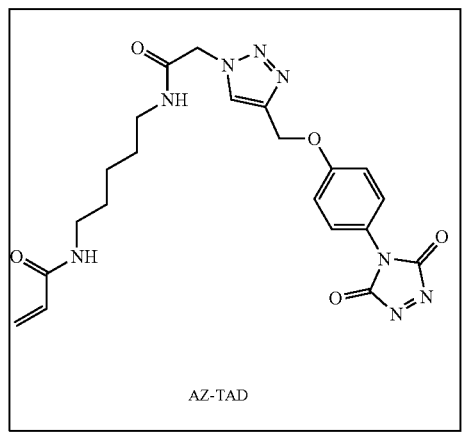
AZ-TAD
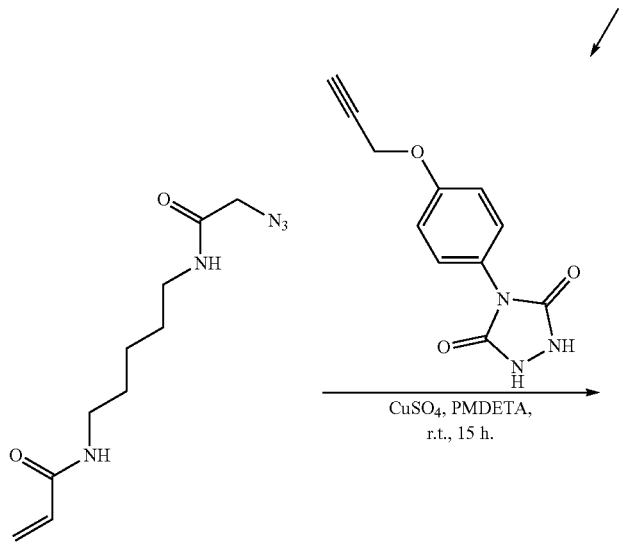
ILMN 'AzAPA'
4-(4-(Prop-2-yn-1-yloxy)phenyl)-1,2,4-triazolidine-3,5-dione
(Sigma: PTAD-Alkyne, 794236-500MG).
CuSO₄, PMDETA, r.t., 15 h.

-continued

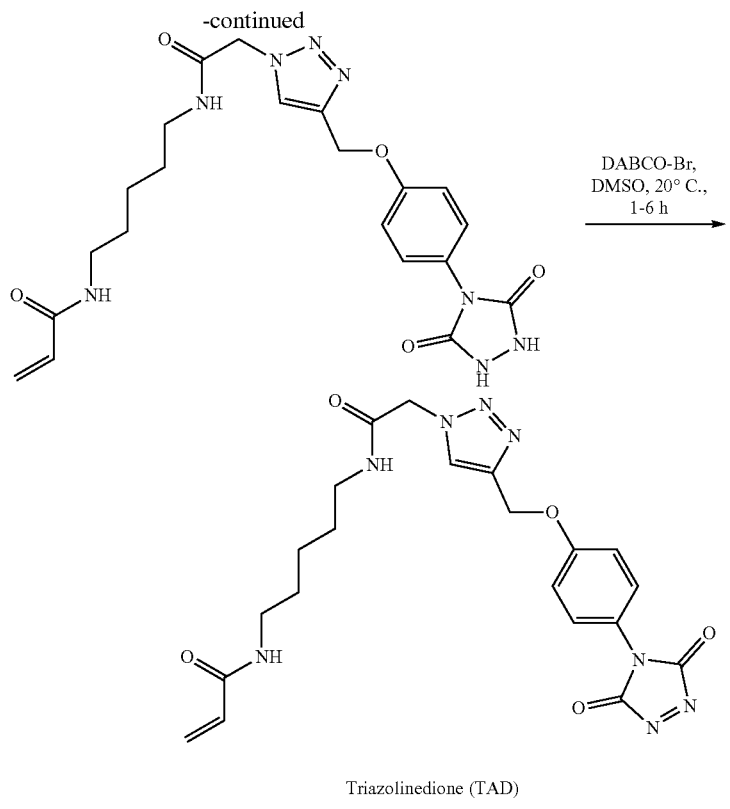

Triazolinedione (TAD)

From these reaction schemes, it may be understood that a diene including a desired functional group, such as an oligonucleotide (e.g., primer), may be reacted with a urazole-protected unsaturated cyclic dione such as TAD that is coupled to a substrate, such as a polymer disposed on a solid support, so as to couple the functional group to the substrate.

ADDITIONAL COMMENTS

It is to be understood that any respective features/examples of each of the aspects of the disclosure as described herein may be implemented together in any appropriate combination, and that any features/examples from any one or more of these aspects may be implemented together with any of the features of the other aspect(s) as described herein in any appropriate combination to achieve the benefits as described herein.

While various illustrative examples are described above, it will be apparent to one skilled in the art that various changes and modifications may be made therein without departing from the invention. The appended claims are intended to cover all such changes and modifications that fall within the true spirit and scope of the invention.

What is claimed is:

1. A method of coupling a functional group to a substrate, the method comprising:
   providing an unsaturated cyclic dione coupled to a substrate; and
   reacting the unsaturated cyclic dione with an indole or indazole including a first functional group to form a first adduct coupling the first functional group to the substrate.

2. The method of claim 1, wherein the unsaturated cyclic dione is:

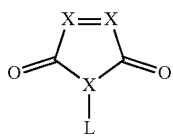

where L comprises a linker to the substrate and each X independently is CH or N.

3. The method of claim 2, wherein the unsaturated cyclic dione is triazolinedione:

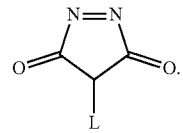

4. The method of claim 2, wherein the unsaturated cyclic dione is maleimide:

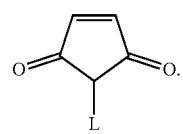

5. The method of claim 2, wherein the unsaturated cyclic dione is 4-cyclopentene-1,3-dione:

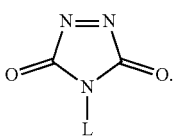

6. The method of claims 1, wherein the indole or indazole is:

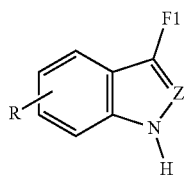

where F1 comprises the first functional group; R is H, an electron withdrawing group, or an electron donating group; and Z is CH or N.

7. The method of claim 6, wherein the indole is 1H-indole:

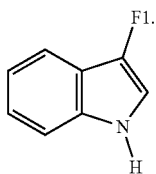

8. The method of claim 6, wherein the indole is 1H-indazole:

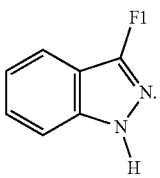

9. The method of claim 6, wherein the first adduct is:

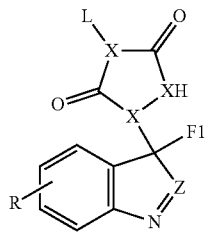

where L comprises a linker to the substrate and each X independently is CH or N.

10. The method of claim 9, wherein the first adduct is:

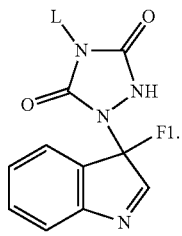

11. The method of claim 1, further comprising heating the first adduct to regenerate the cyclic unsaturated dione coupled to the substrate.

12. The method of claim 1, further comprising reacting the first adduct with a diene including a second functional group to form a second adduct coupling the second functional group to the substrate.

13. The method of claim 12, wherein the diene comprises a 1,3-diene.

14. The method of claim 13, wherein the 1,3-diene is:

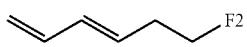

where F2 comprises the second functional group.

15. The method of claim 14, wherein the second adduct is:

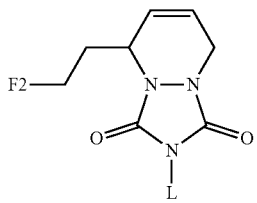

where L comprises a linker to the substrate.

16. The method of claim 12, wherein the second functional group is selected from the group consisting of: an oligonucleotide, a hydrophilic molecule, a hydrophilic macromolecule, a catalyst, and a label.

17. The method of claim 16, wherein the second functional group is an oligonucleotide.

18. The method of claim 1, wherein the first functional group is selected from the group consisting of: an oligonucleotide, a hydrophilic molecule, a hydrophilic macromolecule, a catalyst, and a label.

19. The method of claim 18, wherein the first functional group is an oligonucleotide.

20. The method of claim 1, wherein the substrate comprises a polymer disposed on a solid support.

21. The method of claim 20, wherein the polymer is functionalized to include polyhedral oligomeric silsesquioxane (POSS).

22. The method of claim 1, wherein providing the unsaturated cyclic dione coupled to the substrate comprises:
providing a 4-substituted urazole coupled to the substrate; and
oxidizing the 4-substituted urazole to form a triazolinedione.

* * * * *